US007612254B2

(12) United States Patent
Dhugga et al.

(10) Patent No.: US 7,612,254 B2
(45) Date of Patent: Nov. 3, 2009

(54) MANIPULATION OF PLANT POLYSACCHARIDE SYNTHASES

(75) Inventors: Kanwarpal S. Dhugga, Johnston, IA (US); Dwight T. Tomes, Van Meter, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 328 days.

(21) Appl. No.: 11/494,950

(22) Filed: Jul. 28, 2006

(65) Prior Publication Data

US 2006/0288453 A1 Dec. 21, 2006

Related U.S. Application Data

(63) Continuation of application No. 10/260,046, filed on Sep. 27, 2002, now Pat. No. 7,098,380.

(60) Provisional application No. 60/325,614, filed on Sep. 27, 2001.

(51) Int. Cl.
C12N 15/29 (2006.01)
C12N 15/52 (2006.01)
C12N 15/63 (2006.01)
C12N 15/82 (2006.01)

(52) U.S. Cl. .................. 800/284; 800/298; 536/23.2; 536/23.6; 435/320.1; 435/419

(58) Field of Classification Search .................. None
See application file for complete search history.

(56) References Cited

U.S. PATENT DOCUMENTS 6,194,638 B1  2/2001  Dhugga et al.

FOREIGN PATENT DOCUMENTS

| WO | WO 94/26878 A1 | 11/1994 |
|---|---|---|
| WO | WO 98/00549 | * 1/1998 |
| WO | WO 98/00549 A1 | 1/1998 |
| WO | WO 98/18949 A2 | 5/1998 |
| WO | WO 99/67404 A1 | 12/1999 |
| WO | WO 00/04166 A2 | 1/2000 |
| WO | WO 00/09706 A2 | 2/2000 |
| WO | WO 01/79516 A2 | 10/2001 |

OTHER PUBLICATIONS

Richmond T. et al. Plant Physiology, Oct. 2000; vol. 124, pp. 495-498.*
Arioli T. et al. Science, Jan. 30, 1998; vol. 29, pp. 717-720.*
Hazen S. et al. Cellulose synthase-like genes of rice. Plant Physiology; Feb. 2002, 128:336-340.*
GenBank AF 435643 published Dec. 6, 2001.*
Amor et al., A membrane-associated form of sucrose synthase and its potential role in synthesis of cellulose and callose in plants, Proc. Natl. Acad. Sci. USA (1995) 92:9353-9357.
Amor et al., Evidence for a Cyclic Diguanylic Acid-Dependent Cellulose Synthase in Plants, The Plant Cell (1991) 3:989-995.
Arioli et al., Molecular Analysis of Cellulose Biosynthesis in *Arabidopsis*, Science (1998) 279:717-720.
Aroli et al., Molecular Analysis of Cellulose Biosynthesis in *Arabidopsis*, Science (1998) 279:717-720, Reference No. AF027174, XP-002125689.
Aroli et al., Molecular Analysis of Cellulose Biosynthesis in *Arabidopsis*, Science (1998) 279:717-720, Reference No. 048947, XP-002125688.
Aroli et al., Molecular Analysis of Cellulose Biosynthesis in *Arabidopsis*, Science (1998) 279:717-720, Reference No. 048948, XP-002140697.
Aroli et al., Molecular Analysis of Cellulose Biosynthesis in *Arabidopsis*, Science (1998) 279:717-720, Reference No. AF030052, XP-002140698.
Aroli et al., Molecular Analysis of Cellulose Biosynthesis in *Arabidopsis*, Science (1998) 279:717-720, Reference No. 048946, XP-002140699.
Aroli et al., Molecular Analysis of Cellulose Biosynthesis in *Arabidopsis*, Science (1998) 279:717-720, Reference No. AF027173, XP-002140700.
Cutler et al., Cellulose synthesis: Cloning in silico, Current Biology (1997) 7:R108-R111.
Delmer, Deborah P., Cellulose Biosynthesis: Exciting Times for Difficult Field of Study, Plant Mol. Biol. (1999) 50:245-276.
Dhugga et al., A reversibly glycosylated polypeptide (RGP1) possibly involved in plant cell wall synthesis: Purification, gene cloning, and trans-Golgi localization, Proc. Natl. Acad. Sci. USA (1997) 94:7679-7684.
Dhugga et al., Plant Polypeptides Reversibly Glycosylated by UDP-Glucose, The Journal of Biological Chemistry (1991) 266(32):21977-21984.
Favery et al., Kojak encodes a cellulose synthase-like protein required for root hair cell morphogenesis in *Arabidopsis*, Genes & Development (2001) 15:79-89.
Haigler et al., New hope for old dreams: Evidence that Plant cellulose synthase genes have finally been identified, Proc. Natl. Acad. Sci. USA (1996) 93:12082-12085.
Kerry et al., Differential behaviour of four plant polysaccharide synthases in the presence of organic solvents, Phytochemistry (2001) 57:1055-1060.
Dhugga, Kanwarpal S., Building the wall: genes and enzyme complexes for polysaccharide synthases, Plant Biology (2001) 4:488-493.
Pear et al., Higher plants contain homologs of the bacterial *celA* genes encoding the catalytic subunit of cellulose synthase, Proc. Natl. Acad. Sci. USA (1996) 93:12637-12642.
Richmond et al., Integrative approaches to determining Csl function, Plant Molecular Biology (2001) 47:131-143.
Richmond et al., The Cellulose Synthase Superfamily, Plant Physiology (2000) 124:495-498.
Wu et al., EMBL/GenBank/DDBJ databases, Reference No. 065338, XP-002140701.

* cited by examiner

Primary Examiner—Russell Kallis
(74) Attorney, Agent, or Firm—Pioneer Hi-Bred International, Inc.; Kathryn K. Lappegard

(57) ABSTRACT

The present invention provides compositions and methods for manipulation of plant polysaccharides and plant polysaccharide synthases. Compositions include novel nucleotide sequences encoding polysaccharide synthases polypeptides, and biologically active variants thereof. Further provided are methods for polysaccharide manipulation using the sequences disclosed herein. One method comprises stably incorporating into the genome of a plant cell, a nucleotide sequence of the present invention operably linked to a heterologous promoter and regenerating a stably transformed plant that expresses the nucleotide sequence.

10 Claims, No Drawings

SEQUENCE LISTING

```
<160> NUMBER OF SEQ ID NOS: 30

<210> SEQ ID NO 1
<211> LENGTH: 1910
<212> TYPE: DNA
<213> ORGANISM: Zea mays

<400> SEQUENCE: 1
tcgacccacg cgtccggtcc gttcatctgc tgtcatgtca aatggcccct tcatcctcaa       60
cctcgactgt gatcactatg tctacaactc gcaagctttc cgcgaaggga tgtgcttcat      120
gatggaccgt ggtggcgacc gcattggtta tgtccagttc ccgcagcggt ttgagggcat      180
cgatccatca gatcgctatg ccaaccacaa caccgtcttc ttcgacgtca acatgcgcgc      240
gctggatggt ctcatgggac cagtctatgt tggcactggc tgccttttcc gccgtgttgc      300
cctatatgga tttgaccctc cgcgctccaa ggagcacggt ggctgctgca gctgttgctt      360
cccccagaga cgcaagatca aagcttcagc cgctgcaccg gaggagaccc gggctctaag      420
gatggcagac ttcgacgagg atgaaatgaa catgtcgtcg ttccccaaga agtttggtaa      480
ctcgagcttc ctcatcgact ccattccgat tgctgagttc caagggcgcc cgcttgctga      540
tcaccctggt gtcaagaacg gccgccctcc cggtgctctc actgtccccc gtgaccttct      600
ggatgcatcc acagtcgctg aggccgtcag tgtcatctca tgctggtacg aagacaagac      660
cgagtggggc caccgtgttg gttggatcta tggctcggtg acggaggatg tggtcactgg      720
gtaccggatg cacaaccggg gttggaagtc ggtgtactgt gtcaccaagc gtgacgcctt      780
ccacggcacc gcgcccatca acctgactga ccgtctccac caggtgctcc ggtgggctac      840
tggatcagtg gagatcttct tctcccgcaa caacgcgctg ctggcgagcc gcagaatgaa      900
gttcttgcag aggatcgcgt acctgaacgt gggtatctac ccgttcacgt ccatcttcct      960
gatcgtctac tgcttcctgc cggcgctgtc gctgttctcg gggcagttca tcgtgaagac     1020
gctgaacgtg acgttcctga cgtacctgct ggtgatcacg ctgacgctgt gcctgctggc     1080
ggtgctggag atcaagtggt cggggatcag tctggaggag tggtggcgga acgagcagtt     1140
ctggctgatc ggcggcacga gcgcgcacct ggcggccgtg ctgcagggcc tgctgaaggt     1200
ggtggcgggc atcgagatct ccttcacgct gacgtccaag tcgggcggcg acgacgtgga     1260
cgacgagttc gcggacctgt acatcgtcaa gtggacgtcg ctgatgatcc gcccatcgt     1320 gatcatgatg gtgaacctga tcggcatcgc ggtcgggttc agccgcacca tctacagcga     1380
gatcccgcag tggagcaagc tgctgggcgg cgtcttcttc agcttctggg tgctggcgca     1440
cctgtacccg ttcgccaagg gcctgatggg gcggaggggc cgcacgccaa ccatcgtctt     1500
```

-continued

```
cgtctgggcg ggcctcctct ccatcaccat ctcgctgctg tgggtggcca tcaacccgcc    1560
gtcccagaac cagcagattg gtgggtcgtt cacattcccg tgaaagctct ctgggccaat    1620
ggcggattca tgcatgcttc gtcgcagtgg gatccttgcg ttgctctgca tcagttcctg    1680
gttgcagcgg ttcaatatct gaggacgaag ctgctggggg aatgtgggat ccctgacttg    1740
tcgaaactgg cttactttt ttgttgtcgg aagcttgata atactctta tgatgagcta     1800 tagtagtagt tcttttgttc ttttgttttt gctatatata aaatacatgt tctggtccct    1860
taaaaaaaaa aaaaaaaaa aaaaaaaaaa aaaaaaaaa aaaaaaaaaa               1910
```

<210> SEQ ID NO 2
<211> LENGTH: 522
<212> TYPE: PRT
<213> ORGANISM: Zea mays

<400> SEQUENCE: 2

```
Met Ser Asn Gly Pro Phe Ile Leu Asn Leu Asp Cys Asp His Tyr Val
 1               5                  10                  15

Tyr Asn Ser Gln Ala Phe Arg Glu Gly Met Cys Phe Met Met Asp Arg
                20                  25                  30

Gly Gly Asp Arg Ile Gly Tyr Val Gln Phe Pro Gln Arg Phe Glu Gly
            35                  40                  45

Ile Asp Pro Ser Asp Arg Tyr Ala Asn His Asn Thr Val Phe Phe Asp
        50                  55                  60

Val Asn Met Arg Ala Leu Asp Gly Leu Met Gly Pro Val Tyr Val Gly
 65                  70                  75                  80

Thr Gly Cys Leu Phe Arg Arg Val Ala Leu Tyr Gly Phe Asp Pro Pro
                85                  90                  95

Arg Ser Lys Glu His Gly Gly Cys Cys Ser Cys Cys Phe Pro Gln Arg
            100                 105                 110

Arg Lys Ile Lys Ala Ser Ala Ala Ala Pro Glu Glu Thr Arg Ala Leu
        115                 120                 125

Arg Met Ala Asp Phe Asp Glu Asp Glu Met Asn Met Ser Ser Phe Pro
    130                 135                 140

Lys Lys Phe Gly Asn Ser Ser Phe Leu Ile Asp Ser Ile Pro Ile Ala
145                 150                 155                 160

Glu Phe Gln Gly Arg Pro Leu Ala Asp His Pro Gly Val Lys Asn Gly
                165                 170                 175

Arg Pro Pro Gly Ala Leu Thr Val Pro Arg Asp Leu Leu Asp Ala Ser
            180                 185                 190

Thr Val Ala Glu Ala Val Ser Val Ile Ser Cys Trp Tyr Glu Asp Lys
        195                 200                 205

Thr Glu Trp Gly His Arg Val Gly Trp Ile Tyr Gly Ser Val Thr Glu
    210                 215                 220

Asp Val Val Thr Gly Tyr Arg Met His Asn Arg Gly Trp Lys Ser Val
225                 230                 235                 240

Tyr Cys Val Thr Lys Arg Asp Ala Phe His Gly Thr Ala Pro Ile Asn
                245                 250                 255

Leu Thr Asp Arg Leu His Gln Val Leu Arg Trp Ala Thr Gly Ser Val
            260                 265                 270

Glu Ile Phe Phe Ser Arg Asn Asn Ala Leu Leu Ala Ser Arg Arg Met
        275                 280                 285

Lys Phe Leu Gln Arg Ile Ala Tyr Leu Asn Val Gly Ile Tyr Pro Phe
    290                 295                 300
```

```
Thr Ser Ile Phe Leu Ile Val Tyr Cys Phe Leu Pro Ala Leu Ser Leu
305                 310                 315                 320

Phe Ser Gly Gln Phe Ile Val Lys Thr Leu Asn Val Thr Phe Leu Thr
            325                 330                 335

Tyr Leu Leu Val Ile Thr Leu Thr Leu Cys Leu Leu Ala Val Leu Glu
                340                 345                 350

Ile Lys Trp Ser Gly Ile Ser Leu Glu Glu Trp Trp Arg Asn Glu Gln
        355                 360                 365

Phe Trp Leu Ile Gly Gly Thr Ser Ala His Leu Ala Ala Val Leu Gln
    370                 375                 380

Gly Leu Leu Lys Val Val Ala Gly Ile Glu Ile Ser Phe Thr Leu Thr
385                 390                 395                 400

Ser Lys Ser Gly Gly Asp Val Asp Asp Glu Phe Ala Asp Leu Tyr
            405                 410                 415

Ile Val Lys Trp Thr Ser Leu Met Ile Pro Pro Ile Val Ile Met Met
        420                 425                 430

Val Asn Leu Ile Gly Ile Ala Val Gly Phe Ser Arg Thr Ile Tyr Ser
            435                 440                 445

Glu Ile Pro Gln Trp Ser Lys Leu Leu Gly Gly Val Phe Phe Ser Phe
    450                 455                 460

Trp Val Leu Ala His Leu Tyr Pro Phe Ala Lys Gly Leu Met Gly Arg
465                 470                 475                 480

Arg Gly Arg Thr Pro Thr Ile Val Phe Val Trp Ala Gly Leu Leu Ser
            485                 490                 495

Ile Thr Ile Ser Leu Leu Trp Val Ala Ile Asn Pro Pro Ser Gln Asn
            500                 505                 510

Gln Gln Ile Gly Gly Ser Phe Thr Phe Pro
        515                 520

<210> SEQ ID NO 3
<211> LENGTH: 1569
<212> TYPE: DNA
<213> ORGANISM: Zea mays

<400> SEQUENCE: 3
atgtcaaatg ccccttcat cctcaacctc gactgtgatc actatgtcta caactcgcaa      60
gctttccgcg aagggatgtg cttcatgatg accgtggtg gcgaccgcat tggttatgtc     120
cagttcccgc agcggtttga gggcatcgat ccatcagatc gctatgccaa ccacaacacc     180
gtcttcttcg acgtcaacat gcgcgcgctg gatggtctca tgggaccagt ctatgttggc     240
actggctgcc ttttccgccg tgttgcccta tatggatttg accctccgcg ctccaaggag     300
cacggtggct gctgcagctg ttgcttcccc cagagacgca agatcaaagc ttcagccgct     360
gcaccggagg agacccgggc tctaaggatg gcagacttcg acgaggatga aatgaacatg     420
tcgtcgttcc ccaagaagtt tggtaactcg agcttcctca tcgactccat tccgattgct     480
gagttccaag gcgcccgct tgctgataca cctggtgtca agaacggccg ccctcccggt     540
gctctcactg tccccgtga ccttctggat gcatccacag tcgctgaggc cgtcagtgtc     600
atctcatgct ggtacgaaga caagaccgag tggggccacc gtgttggttg gatctatggc     660
tcggtgacgg aggatgtggt cactgggtac cggatgcaca accggggttg gaagtcggtg     720
tactgtgtca ccaagcgtga cgccttccac ggcaccgcgc ccatcaacct gactgaccgt     780
ctccaccagg tgctccggtg ggctactgga tcagtggaga tcttcttctc ccgcaacaac     840
gcgctgctgg cgagccgcag aatgaagttc ttgcagagga tcgcgtacct gaacgtgggt     900
```

```
atctacccgt tcacgtccat cttcctgatc gtctactgct tcctgccggc gctgtcgctg      960
ttctcggggc agttcatcgt gaagacgctg aacgtgacgt tcctgacgta cctgctggtg     1020
atcacgctga cgctgtgcct gctggcggtg ctggagatca agtggtcggg gatcagtctg     1080
gaggagtggt ggcggaacga gcagttctgg ctgatcggcg gcacgagcgc gcacctggcg     1140
gccgtgctgc agggcctgct gaaggtggtg gcgggcatcg agatctcctt cacgctgacg     1200
tccaagtcgg gcggcgacga cgtggacgac gagttcgcgg acctgtacat cgtcaagtgg     1260
acgtcgctga tgatcccgcc catcgtgatc atgatggtga acctgatcgg catcgcggtc     1320
gggttcagcc gcaccatcta cagcgagatc ccgcagtgga gcaagctgct gggcggcgtc     1380
ttcttcagct ctgggtgctg gcgcacctg tacccgttcg ccaagggcct gatggggcgg     1440
aggggccgca cgccaaccat cgtcttcgtc tgggcgggcc tcctctccat caccatctcg     1500
ctgctgtggg tggccatcaa cccgccgtcc cagaaccagc agattggtgg gtcgttcaca     1560
ttcccgtga                                                             1569

<210> SEQ ID NO 4
<211> LENGTH: 522
<212> TYPE: PRT
<213> ORGANISM: Zea mays

<400> SEQUENCE: 4

Met Ser Asn Gly Pro Phe Ile Leu Asn Leu Asp Cys Asp His Tyr Val
 1               5                  10                  15

Tyr Asn Ser Gln Ala Phe Arg Glu Gly Met Cys Phe Met Met Asp Arg
            20                  25                  30

Gly Gly Asp Arg Ile Gly Tyr Val Gln Phe Pro Gln Arg Phe Glu Gly
        35                  40                  45

Ile Asp Pro Ser Asp Arg Tyr Ala Asn His Asn Thr Val Phe Phe Asp
    50                  55                  60

Val Asn Met Arg Ala Leu Asp Gly Leu Met Gly Pro Val Tyr Val Gly
65                  70                  75                  80

Thr Gly Cys Leu Phe Arg Arg Val Ala Leu Tyr Gly Phe Asp Pro Pro
                85                  90                  95

Arg Ser Lys Glu His Gly Gly Cys Cys Ser Cys Cys Phe Pro Gln Arg
           100                 105                 110

Arg Lys Ile Lys Ala Ser Ala Ala Ala Pro Glu Glu Thr Arg Ala Leu
       115                 120                 125

Arg Met Ala Asp Phe Asp Glu Asp Glu Met Asn Met Ser Ser Phe Pro
   130                 135                 140

Lys Lys Phe Gly Asn Ser Ser Phe Leu Ile Asp Ser Ile Pro Ile Ala
145                 150                 155                 160

Glu Phe Gln Gly Arg Pro Leu Ala Asp His Pro Gly Val Lys Asn Gly
               165                  170                 175

Arg Pro Pro Gly Ala Leu Thr Val Pro Arg Asp Leu Leu Asp Ala Ser
           180                 185                 190

Thr Val Ala Glu Ala Val Ser Val Ile Ser Cys Trp Tyr Glu Asp Lys
       195                 200                 205

Thr Glu Trp Gly His Arg Val Gly Trp Ile Tyr Gly Ser Val Thr Glu
   210                 215                 220

Asp Val Val Thr Gly Tyr Arg Met His Asn Arg Gly Trp Lys Ser Val
225                 230                 235                 240

Tyr Cys Val Thr Lys Arg Asp Ala Phe His Gly Thr Ala Pro Ile Asn
               245                 250                 255
```

```
Leu Thr Asp Arg Leu His Gln Val Leu Arg Trp Ala Thr Gly Ser Val
            260                 265                 270
Glu Ile Phe Phe Ser Arg Asn Asn Ala Leu Leu Ala Ser Arg Arg Met
            275                 280                 285
Lys Phe Leu Gln Arg Ile Ala Tyr Leu Asn Val Gly Ile Tyr Pro Phe
            290                 295                 300
Thr Ser Ile Phe Leu Ile Val Tyr Cys Phe Leu Pro Ala Leu Ser Leu
305                 310                 315                 320
Phe Ser Gly Gln Phe Ile Val Lys Thr Leu Asn Val Thr Phe Leu Thr
                    325                 330                 335
Tyr Leu Leu Val Ile Thr Leu Thr Leu Cys Leu Leu Ala Val Leu Glu
                    340                 345                 350
Ile Lys Trp Ser Gly Ile Ser Leu Glu Glu Trp Trp Arg Asn Glu Gln
                    355                 360                 365
Phe Trp Leu Ile Gly Gly Thr Ser Ala His Leu Ala Ala Val Leu Gln
            370                 375                 380
Gly Leu Leu Lys Val Val Ala Gly Ile Glu Ile Ser Phe Thr Leu Thr
385                 390                 395                 400
Ser Lys Ser Gly Gly Asp Asp Val Asp Asp Glu Phe Ala Asp Leu Tyr
                    405                 410                 415
Ile Val Lys Trp Thr Ser Leu Met Ile Pro Pro Ile Val Ile Met Met
            420                 425                 430
Val Asn Leu Ile Gly Ile Ala Val Gly Phe Ser Arg Thr Ile Tyr Ser
            435                 440                 445
Glu Ile Pro Gln Trp Ser Lys Leu Leu Gly Gly Val Phe Phe Ser Phe
            450                 455                 460
Trp Val Leu Ala His Leu Tyr Pro Phe Ala Lys Gly Leu Met Gly Arg
465                 470                 475                 480
Arg Gly Arg Thr Pro Thr Ile Val Phe Val Trp Ala Gly Leu Leu Ser
                    485                 490                 495
Ile Thr Ile Ser Leu Leu Trp Val Ala Ile Asn Pro Pro Ser Gln Asn
            500                 505                 510
Gln Gln Ile Gly Gly Ser Phe Thr Phe Pro
            515                 520
```

<210> SEQ ID NO 5
<211> LENGTH: 1673
<212> TYPE: DNA
<213> ORGANISM: Zea mays

<400> SEQUENCE: 5

```
tcttcgccgc cgcctacgcg gcctggatgc gcgcccgcct cgactacctc gcgccgccgc      60
tgcagttcct aaccaacgcc tgcgtcctcc tcttcctggt ccagagcgtc gaccgcctcg     120
tgctctgcct cggctgcttc tggatcaagc tcaagggcgt caggcccgtg ccgccgctgc     180
ccgccgacaa ggaggacgtc gaggccggtc ccgacggcgt ccccatggtg ctcgtgcaga     240
tgcccatgtg caatgagaga gaggtgtatc aacaatcaat gcggccgtg tgcaaccttg      300
actggcccaa atccaacttc ttggtccaag tgttggatga ctccgacgac ccactcacaa     360
aggctctaat cagagaagaa gtggccaaat ggcaacagca gggtgcccgg attgtgtacc     420
ggcaccgggt gatccgggat ggctacaagg ctggaaacct gaaatcagcc atgaactgca     480
gttacgtgaa agactatgag ttcgttgtca tcttcgatgc tgatttccaa ccacaggcgg     540
acttcctgaa gcgcaccgtg ccccatttca agggaaagga tgacgtcggg ttggttcagg     600
```

```
cgagatggtc gttcgtaaac aaggatgaga acttgctgac caggcttcag aacataaatc    660
tttgcttcca cttcgaggtg gagcagcagg tgaacggggc gtttctcaac ttcttcgggt    720
tcaatggcac cgcgggagtc tggagaatca aggcgcttga ggagtctgga ggatggatgg    780
agaggacgac ggtggaggac atggacatag ctgttcgagc gcacctcaaa gggtggaagt    840
ttctctttct aaacgatgtc gagtgtcagt gtgaattgcc agaatcgtat gaagcgtaca    900
gaaagcagca gcaccggtgg cactcaggtc ccatgcaatt gtttaggctc tgctttgtgg    960
atataatcaa atctaagatc ggtttctgga agaagttcaa cctcatattc ctcttcttcc   1020
tgctccggaa gctgatacta cccttctact ccttcaccct cttctgcatc atcctcccga   1080
tgacgatgtt cgtgccggag ccgagctcc ccgactgggt ggtgtgctac gtcccggccc   1140
tgatgtccct gctgaacatc ctgccgtccc caagtcgtt ccccttcatc atcccgtacc   1200
tgctcttcga gaacaccatg tccgtgacca gttcaacgc gatgatctcc gggctgttcc   1260
agctggggag cgcgtacgag tgggtggtga ccaagaagtc gggccgctcg tcggagggcg   1320
acctcatcgc gctggccccg cccaaggagc ctgtgaagca cgcgacgagg acgggctccg   1380
cgccgaacct cgacgccgtc gccaaggagg agcaacagca gcagcagctg gcggcgtcga   1440
ggaaggacgc cgccgcgaag aagaaggaga agcacaaccg gatatacaag aaggagctgg   1500
cgctgtcgat gctgctcctg accgcggccg cccggagcct gctgtcgaag catggcatac   1560
acttctactt cctcctgttc cagggcgtgt ccttcttgct agtaggcctt gacctcatag   1620
gcgagcaagt cgagtgaaat gtgtataaca ggaaactgat acgtgtggga aaa            1673

<210> SEQ ID NO 6
<211> LENGTH: 536
<212> TYPE: PRT
<213> ORGANISM: Zea mays

<400> SEQUENCE: 6

Met Arg Ala Arg Leu Asp Tyr Leu Ala Pro Pro Leu Gln Phe Leu Thr
  1               5                  10                  15

Asn Ala Cys Val Leu Leu Phe Leu Val Gln Ser Val Asp Arg Leu Val
             20                  25                  30

Leu Cys Leu Gly Cys Phe Trp Ile Lys Leu Lys Gly Val Arg Pro Val
         35                  40                  45

Pro Pro Leu Pro Ala Asp Lys Glu Asp Val Glu Ala Gly Pro Asp Gly
     50                  55                  60

Val Pro Met Val Leu Val Gln Met Pro Met Cys Asn Glu Arg Glu Val
 65                  70                  75                  80

Tyr Gln Gln Ser Ile Ala Ala Val Cys Asn Leu Asp Trp Pro Lys Ser
                 85                  90                  95

Asn Phe Leu Val Gln Val Leu Asp Asp Ser Asp Pro Leu Thr Lys
             100                 105                 110

Ala Leu Ile Arg Glu Glu Val Ala Lys Trp Gln Gln Gly Ala Arg
         115                 120                 125

Ile Val Tyr Arg His Arg Val Ile Arg Asp Gly Tyr Lys Ala Gly Asn
     130                 135                 140

Leu Lys Ser Ala Met Asn Cys Ser Tyr Val Lys Asp Tyr Glu Phe Val
145                 150                 155                 160

Val Ile Phe Asp Ala Asp Phe Gln Pro Gln Ala Asp Phe Leu Lys Arg
                 165                 170                 175

Thr Val Pro His Phe Lys Gly Lys Asp Val Gly Leu Val Gln Ala
             180                 185                 190
```

Arg Trp Ser Phe Val Asn Lys Asp Glu Asn Leu Leu Thr Arg Leu Gln
            195                 200                 205

Asn Ile Asn Leu Cys Phe His Phe Glu Val Glu Gln Gln Val Asn Gly
210                 215                 220

Ala Phe Leu Asn Phe Phe Gly Phe Asn Gly Thr Ala Gly Val Trp Arg
225                 230                 235                 240

Ile Lys Ala Leu Glu Glu Ser Gly Gly Trp Met Glu Arg Thr Thr Val
            245                 250                 255

Glu Asp Met Asp Ile Ala Val Arg Ala His Leu Lys Gly Trp Lys Phe
                260                 265                 270

Leu Phe Leu Asn Asp Val Glu Cys Gln Cys Glu Leu Pro Glu Ser Tyr
            275                 280                 285

Glu Ala Tyr Arg Lys Gln Gln His Arg Trp His Ser Gly Pro Met Gln
        290                 295                 300

Leu Phe Arg Leu Cys Phe Val Asp Ile Ile Lys Ser Lys Ile Gly Phe
305                 310                 315                 320

Trp Lys Lys Phe Asn Leu Ile Phe Leu Phe Phe Leu Leu Arg Lys Leu
                325                 330                 335

Ile Leu Pro Phe Tyr Ser Phe Thr Leu Phe Cys Ile Ile Leu Pro Met
            340                 345                 350

Thr Met Phe Val Pro Glu Ala Glu Leu Pro Asp Trp Val Val Cys Tyr
        355                 360                 365

Val Pro Ala Leu Met Ser Leu Leu Asn Ile Leu Pro Ser Pro Lys Ser
    370                 375                 380

Phe Pro Phe Ile Ile Pro Tyr Leu Leu Phe Glu Asn Thr Met Ser Val
385                 390                 395                 400

Thr Lys Phe Asn Ala Met Ile Ser Gly Leu Phe Gln Leu Gly Ser Ala
                405                 410                 415

Tyr Glu Trp Val Val Thr Lys Lys Ser Gly Arg Ser Ser Glu Gly Asp
            420                 425                 430

Leu Ile Ala Leu Ala Pro Pro Lys Glu Pro Val Lys His Ala Thr Arg
        435                 440                 445

Thr Gly Ser Ala Pro Asn Leu Asp Ala Val Ala Lys Glu Glu Gln Gln
    450                 455                 460

Gln Gln Gln Leu Ala Ala Ser Arg Lys Asp Ala Ala Lys Lys Lys
465                 470                 475                 480

Glu Lys His Asn Arg Ile Tyr Lys Lys Glu Leu Ala Leu Ser Met Leu
                485                 490                 495

Leu Leu Thr Ala Ala Ala Arg Ser Leu Leu Ser Lys His Gly Ile His
            500                 505                 510

Phe Tyr Phe Leu Leu Phe Gln Gly Val Ser Phe Leu Leu Val Gly Leu
        515                 520                 525

Asp Leu Ile Gly Glu Gln Val Glu
    530                 535

<210> SEQ ID NO 7
<211> LENGTH: 1611
<212> TYPE: DNA
<213> ORGANISM: Zea mays

<400> SEQUENCE: 7
atgcgcgccc gcctcgacta cctcgcgccg ccgctgcagt tcctaaccaa cgcctgcgtc      60
ctcctcttcc tggtccagag cgtcgaccgc tcgtgctct gcctcggctg cttctggatc     120
aagctcaagg gcgtcaggcc cgtgccgccg ctgcccgccg acaaggagga cgtcgaggcc     180

-continued

```
ggtcccgacg gcgtcccat ggtgctcgtg cagatgccca tgtgcaatga gagagaggtg    240
tatcaacaat caattgcggc cgtgtgcaac cttgactggc ccaaatccaa cttcttggtc    300
caagtgttgg atgactccga cgacccactc acaaaggctc taatcagaga agaagtggcc    360
aaatggcaac agcagggtgc ccggattgtg taccggcacc gggtgatccg ggatggctac    420
aaggctggaa acctgaaatc agccatgaac tgcagttacg tgaaagacta tgagttcgtt    480
gtcatcttcg atgctgattt ccaaccacag gcggacttcc tgaagcgcac cgtgccccat    540
ttcaagggaa aggatgacgt cgggttggtt caggcgagat ggtcgttcgt aaacaaggat    600
gagaacttgc tgaccaggct tcagaacata aatctttgct tccacttcga ggtggagcag    660
caggtgaacg ggcgtttct caacttcttc gggttcaatg gcaccgcggg agtctggaga    720
atcaaggcgc ttgaggagtc tggaggatgg atggagagga cgacggtgga ggacatggac    780
atagctgttc gagcgcacct caaagggtgg aagtttctct ttctaaacga tgtcgagtgt    840
cagtgtgaat tgccagaatc gtatgaagcg tacagaaagc agcagcaccg gtggcactca    900
ggtcccatgc aattgtttag ctctgctttt gtggatataa tcaaatctaa gatcggtttc    960
tggaagaagt tcaacctcat attcctcttc ttcctgctcc ggaagctgat actacccttc    1020
tactccttca ccctcttctg catcatcctc ccgatgacga tgttcgtgcc ggaggccgag    1080
ctccccgact gggtggtgtg ctacgtcccg gccctgatgt ccctgctgaa catcctgccg    1140
tcccccaagt cgttccccctt catcatcccg tacctgctct tcgagaacac catgtccgtg    1200
accaagttca cgcgatgat ctccgggctg ttccagctgg ggagcgcgta cgagtgggtg    1260
gtgaccaaga agtcgggccg ctcgtcggag ggcgacctca tcgcgctggc cccgcccaag    1320
gagcctgtga agcacgcgac gaggacgggc tccgcgccga acctgacgcg cgtcgccaag    1380
gaggagcaac agcagcagca gctggcggcg tcgaggaagg acgccgccgc gaagaagaag    1440
gagaagcaca accggatata caagaaggag ctggcgctgt cgatgctgct cctgaccgcg    1500
gccgcccgga gcctgctgtc gaagcatggc atacacttct acttcctcct gttccagggc    1560
gtgtccttct tgctagtagg ccttgacctc ataggcgagc aagtcgagtg a    1611
```

<210> SEQ ID NO 8
<211> LENGTH: 536
<212> TYPE: PRT
<213> ORGANISM: Zea mays

<400> SEQUENCE: 8

```
Met Arg Ala Arg Leu Asp Tyr Leu Ala Pro Leu Gln Phe Leu Thr
 1               5                  10                  15

Asn Ala Cys Val Leu Leu Phe Leu Val Gln Ser Val Asp Arg Leu Val
                20                  25                  30

Leu Cys Leu Gly Cys Phe Trp Ile Lys Leu Lys Gly Val Arg Pro Val
            35                  40                  45

Pro Pro Leu Pro Ala Asp Lys Glu Asp Val Glu Ala Gly Pro Asp Gly
        50                  55                  60

Val Pro Met Val Leu Val Gln Met Pro Met Cys Asn Glu Arg Glu Val
 65                  70                  75                  80

Tyr Gln Gln Ser Ile Ala Ala Val Cys Asn Leu Asp Trp Pro Lys Ser
                85                  90                  95

Asn Phe Leu Val Gln Val Leu Asp Asp Ser Asp Asp Pro Leu Thr Lys
                100                 105                 110

Ala Leu Ile Arg Glu Glu Val Ala Lys Trp Gln Gln Gln Gly Ala Arg
            115                 120                 125
```

```
Ile Val Tyr Arg His Arg Val Ile Arg Asp Gly Tyr Lys Ala Gly Asn
130                 135                 140

Leu Lys Ser Ala Met Asn Cys Ser Tyr Val Lys Asp Tyr Glu Phe Val
145                 150                 155                 160

Val Ile Phe Asp Ala Asp Phe Gln Pro Gln Ala Asp Phe Leu Lys Arg
                165                 170                 175

Thr Val Pro His Phe Lys Gly Lys Asp Asp Val Gly Leu Val Gln Ala
                180                 185                 190

Arg Trp Ser Phe Val Asn Lys Asp Glu Asn Leu Leu Thr Arg Leu Gln
            195                 200                 205

Asn Ile Asn Leu Cys Phe His Phe Glu Val Glu Gln Gln Val Asn Gly
210                 215                 220

Ala Phe Leu Asn Phe Phe Gly Phe Asn Gly Thr Ala Gly Val Trp Arg
225                 230                 235                 240

Ile Lys Ala Leu Glu Glu Ser Gly Gly Trp Met Glu Arg Thr Thr Val
                245                 250                 255

Glu Asp Met Asp Ile Ala Val Arg Ala His Leu Lys Gly Trp Lys Phe
                260                 265                 270

Leu Phe Leu Asn Asp Val Glu Cys Gln Cys Glu Leu Pro Glu Ser Tyr
            275                 280                 285

Glu Ala Tyr Arg Lys Gln Gln His Arg Trp His Ser Gly Pro Met Gln
290                 295                 300

Leu Phe Arg Leu Cys Phe Val Asp Ile Ile Lys Ser Lys Ile Gly Phe
305                 310                 315                 320

Trp Lys Lys Phe Asn Leu Ile Phe Leu Phe Phe Leu Leu Arg Lys Leu
                325                 330                 335

Ile Leu Pro Phe Tyr Ser Phe Thr Leu Phe Cys Ile Ile Leu Pro Met
                340                 345                 350

Thr Met Phe Val Pro Glu Ala Glu Leu Pro Asp Trp Val Val Cys Tyr
            355                 360                 365

Val Pro Ala Leu Met Ser Leu Leu Asn Ile Leu Pro Ser Pro Lys Ser
370                 375                 380

Phe Pro Phe Ile Ile Pro Tyr Leu Leu Phe Glu Asn Thr Met Ser Val
385                 390                 395                 400

Thr Lys Phe Asn Ala Met Ile Ser Gly Leu Phe Gln Leu Gly Ser Ala
                405                 410                 415

Tyr Glu Trp Val Val Thr Lys Lys Ser Gly Arg Ser Ser Glu Gly Asp
                420                 425                 430

Leu Ile Ala Leu Ala Pro Pro Lys Glu Pro Val Lys His Ala Thr Arg
            435                 440                 445

Thr Gly Ser Ala Pro Asn Leu Asp Ala Val Ala Lys Glu Glu Gln Gln
            450                 455                 460

Gln Gln Gln Leu Ala Ala Ser Arg Lys Asp Ala Ala Lys Lys
465                 470                 475                 480

Glu Lys His Asn Arg Ile Tyr Lys Lys Glu Leu Ala Leu Ser Met Leu
                485                 490                 495

Leu Leu Thr Ala Ala Ala Arg Ser Leu Leu Ser Lys His Gly Ile His
            500                 505                 510

Phe Tyr Phe Leu Leu Phe Gln Gly Val Ser Phe Leu Leu Val Gly Leu
        515                 520                 525

Asp Leu Ile Gly Glu Gln Val Glu
530                 535
```

<210> SEQ ID NO 9
<211> LENGTH: 1221
<212> TYPE: DNA
<213> ORGANISM: Zea mays

<400> SEQUENCE: 9

```
ccacgcgtcc gggcaggagc tctgaagaaa ggaatggaat gtgactatgc atggcaaagc      60
gaatacattg ctatatttga tgctgatttc caacctgaac cagattttct gctccaaact     120
gtcccattcc ttctgcacaa tccagaagtt gcacttgttc aagctcggtg gtccttcgtg     180
aatgacacga caagcctgct gacaagggta caaaagatgt tttacgacta ccacttcaaa     240
gttgaacaag aagcaggatc agcgaccttt gccttcttca gtttcaacgg aactgctgga     300
gtgtggcgta caggagccat aagagatgca ggaggttgga aggaccgaac tacagttgaa     360
gacatggact tggcggttcg agcaacacta aagggctgga aattcgtata tgttggagac     420
gttagagtca agagtgaact gccgtccact tacaaggcct actgtcggca gcaattccgg     480
tggtctagtg gtggtgcaaa cttattccgt aagatggcaa aggatgtttt gtttgccaag     540
gatatatcac tcgtcaagaa gttctatatg ctctatagct tcttctttgt gaggagagtt     600
gtagcgccga cggctgcctg tattctctac aatgtcatca tccccatctc agtcacaatc     660
ccggagcttt acctaccagt gtggggtgtt gcctatattc ccatggtgct accgtggtc      720
acagctataa gacatccaaa aaatctacac atactgccat tttggatttt gtttgagagt     780
gtgatgacat tgcatcggat gagggctgcg atgactggac tgctggagct agaaggattc     840
aaccagtgga ttgtgacaaa gaaggtgggg aatgatctcg aggacactga agttcctttg     900
cttcagaaaa cccggaaaag gctgagagac agagtcaatc tccccgagat tggattttcg     960
gtgtttctct tcctctgtgc atcatacaac ctggtgttcc atgggaaaac aagctactac    1020
ttatatatgt accttcaggg gttagcattt ctgttactag ggtttaactt cactggcaat    1080
tgttcttgct accaatgata gcatgtcaaa gctgtacgaa ttgctgattg atattcattt    1140
tctggtcatg cgttcgtawt gaaaaaaaaa aaaaaaaaa aaaaaaaaaa aaaaaaaaa     1200
aaaaaaaaaa aaaaaaaaaa g                                             1221
```

<210> SEQ ID NO 10
<211> LENGTH: 354
<212> TYPE: PRT
<213> ORGANISM: Zea mays

<400> SEQUENCE: 10

```
Met Glu Cys Asp Tyr Ala Trp Gln Ser Glu Tyr Ile Ala Ile Phe Asp
  1               5                  10                  15

Ala Asp Phe Gln Pro Glu Pro Asp Phe Leu Leu Gln Thr Val Pro Phe
             20                  25                  30

Leu Leu His Asn Pro Glu Val Ala Leu Val Gln Ala Arg Trp Ser Phe
         35                  40                  45

Val Asn Asp Thr Thr Ser Leu Leu Thr Arg Val Gln Lys Met Phe Tyr
     50                  55                  60

Asp Tyr His Phe Lys Val Glu Gln Glu Ala Gly Ser Ala Thr Phe Ala
 65                  70                  75                  80

Phe Phe Ser Phe Asn Gly Thr Ala Gly Val Trp Arg Thr Gly Ala Ile
                 85                  90                  95

Arg Asp Ala Gly Gly Trp Lys Asp Arg Thr Thr Val Glu Asp Met Asp
            100                 105                 110
```

```
Leu Ala Val Arg Ala Thr Leu Lys Gly Trp Lys Phe Val Tyr Val Gly
        115                 120                 125

Asp Val Arg Val Lys Ser Glu Leu Pro Ser Thr Tyr Lys Ala Tyr Cys
        130                 135                 140

Arg Gln Gln Phe Arg Trp Ser Ser Gly Gly Ala Asn Leu Phe Arg Lys
145                 150                 155                 160

Met Ala Lys Asp Val Leu Phe Ala Lys Asp Ile Ser Leu Val Lys Lys
                165                 170                 175

Phe Tyr Met Leu Tyr Ser Phe Phe Val Arg Arg Val Val Ala Pro
        180                 185                 190

Thr Ala Ala Cys Ile Leu Tyr Asn Val Ile Pro Ile Ser Val Thr
        195                 200                 205

Ile Pro Glu Leu Tyr Leu Pro Val Trp Gly Val Ala Tyr Ile Pro Met
        210                 215                 220

Val Leu Thr Val Val Thr Ala Ile Arg His Pro Lys Asn Leu His Ile
225                 230                 235                 240

Leu Pro Phe Trp Ile Leu Phe Glu Ser Val Met Thr Leu His Arg Met
                245                 250                 255

Arg Ala Ala Met Thr Gly Leu Leu Glu Leu Glu Gly Phe Asn Gln Trp
                260                 265                 270

Ile Val Thr Lys Lys Val Gly Asn Asp Leu Glu Asp Thr Glu Val Pro
        275                 280                 285

Leu Leu Gln Lys Thr Arg Lys Arg Leu Arg Asp Arg Val Asn Leu Pro
        290                 295                 300

Glu Ile Gly Phe Ser Val Phe Leu Phe Leu Cys Ala Ser Tyr Asn Leu
305                 310                 315                 320

Val Phe His Gly Lys Thr Ser Tyr Tyr Leu Tyr Met Tyr Leu Gln Gly
                325                 330                 335

Leu Ala Phe Leu Leu Leu Gly Phe Asn Phe Thr Gly Asn Cys Ser Cys
                340                 345                 350

Tyr Gln

<210> SEQ ID NO 11
<211> LENGTH: 1065
<212> TYPE: DNA
<213> ORGANISM: Zea mays

<400> SEQUENCE: 11
atggaatgtg actatgcatg gcaaagcgaa tacattgcta tatttgatgc tgatttccaa        60
cctgaaccag attttctgct ccaaactgtc ccattccttc tgcacaatcc agaagttgca       120
cttgttcaag ctcggtggtc cttcgtgaat gacacgacaa gcctgctgac aagggtacaa       180
aagatgtttt acgactacca cttcaaagtt gaacaagaag caggatcagc gacctttgcc       240
ttcttcagtt tcaacggaac tgctggagtg tggcgtacag gagccataag agatgcagga       300
ggttggaagg accgaactac agttgaagac atggacttgg cggttcgagc aacactaaag       360
ggctggaaat tcgtatatgt tggagacgtt agagtcaaga gtgaactgcc gtccacttac       420
aaggcctact gtcggcagca attccggtgg tctagtggtg gtgcaaactt attccgtaag       480
atggcaaagg atgttttgtt tgccaaggat atatcactcg tcaagaagtt ctatatgctc       540
tatagcttct ctttgtgag gagagttgta gcgccgacgg ctgcctgtat tctctacaat       600
gtcatcatcc ccatctcagt cacaatcccg gagctttacc taccagtgtg gggtgttgcc       660
tatattccca tggtgcttac cgtggtcaca gctataagac atccaaaaaa tctacacata       720
```

```
ctgccatttt ggattttgtt tgagagtgtg atgacattgc atcggatgag ggctgcgatg    780
actggactgc tggagctaga aggattcaac cagtggattg tgacaaagaa ggtggggaat    840
gatctcgagg acactgaagt tcctttgctt cagaaaaccc ggaaaaggct gagagacaga    900
gtcaatctcc ccgagattgg attttcggtg tttctcttcc tctgtgcatc atacaacctg    960
gtgttccatg ggaaaacaag ctactactta tatatgtacc ttcagggggtt agcatttctg   1020 ttactagggt ttaacttcac tggcaattgt tcttgctacc aatga                   1065
```

<210> SEQ ID NO 12
<211> LENGTH: 354
<212> TYPE: PRT
<213> ORGANISM: Zea mays

<400> SEQUENCE: 12

```
Met Glu Cys Asp Tyr Ala Trp Gln Ser Glu Tyr Ile Ala Ile Phe Asp
 1               5                  10                  15

Ala Asp Phe Gln Pro Glu Pro Asp Phe Leu Leu Gln Thr Val Pro Phe
            20                  25                  30

Leu Leu His Asn Pro Glu Val Ala Leu Val Gln Ala Arg Trp Ser Phe
        35                  40                  45

Val Asn Asp Thr Thr Ser Leu Leu Thr Arg Val Gln Lys Met Phe Tyr
    50                  55                  60

Asp Tyr His Phe Lys Val Glu Gln Glu Ala Gly Ser Ala Thr Phe Ala
65                  70                  75                  80

Phe Phe Ser Phe Asn Gly Thr Ala Gly Val Trp Arg Thr Gly Ala Ile
                85                  90                  95

Arg Asp Ala Gly Gly Trp Lys Asp Arg Thr Thr Val Glu Asp Met Asp
            100                 105                 110

Leu Ala Val Arg Ala Thr Leu Lys Gly Trp Lys Phe Val Tyr Val Gly
        115                 120                 125

Asp Val Arg Val Lys Ser Glu Leu Pro Ser Thr Tyr Lys Ala Tyr Cys
    130                 135                 140

Arg Gln Gln Phe Arg Trp Ser Ser Gly Gly Ala Asn Leu Phe Arg Lys
145                 150                 155                 160

Met Ala Lys Asp Val Leu Phe Ala Lys Asp Ile Ser Leu Val Lys Lys
                165                 170                 175

Phe Tyr Met Leu Tyr Ser Phe Phe Val Arg Arg Val Val Ala Pro
            180                 185                 190

Thr Ala Ala Cys Ile Leu Tyr Asn Val Ile Pro Ile Ser Val Thr
        195                 200                 205

Ile Pro Glu Leu Tyr Leu Pro Val Trp Gly Val Ala Tyr Ile Pro Met
    210                 215                 220

Val Leu Thr Val Val Thr Ala Ile Arg His Pro Lys Asn Leu His Ile
225                 230                 235                 240

Leu Pro Phe Trp Ile Leu Phe Glu Ser Val Met Thr Leu His Arg Met
                245                 250                 255

Arg Ala Ala Met Thr Gly Leu Leu Glu Leu Glu Gly Phe Asn Gln Trp
            260                 265                 270

Ile Val Thr Lys Lys Val Gly Asn Asp Leu Glu Asp Thr Glu Val Pro
        275                 280                 285

Leu Leu Gln Lys Thr Arg Lys Arg Leu Arg Asp Arg Val Asn Leu Pro
    290                 295                 300

Glu Ile Gly Phe Ser Val Phe Leu Phe Leu Cys Ala Ser Tyr Asn Leu
305                 310                 315                 320
```

```
Val Phe His Gly Lys Thr Ser Tyr Tyr Leu Tyr Met Tyr Leu Gln Gly
            325                 330                 335

Leu Ala Phe Leu Leu Leu Gly Phe Asn Phe Thr Gly Asn Cys Ser Cys
            340                 345                 350

Tyr Gln

<210> SEQ ID NO 13
<211> LENGTH: 1899
<212> TYPE: DNA
<213> ORGANISM: Zea mays

<400> SEQUENCE: 13
gcctcttcgc cgccgcctac gcggcctgga tgcgcgcccg cctcgactac ctcgcgccgc     60
cgctgcagtt cctaaccaac gcctgcgtcc tcctcttcct ggtccagagc gtcgaccgcc    120
tcgtgctctg cctcggctgc ttctggatca agctcaaggg cgtcaggccc gtgccgccgc    180
tgcccgccga caaggaggac gtcgaggccg tcccgacgg cgtccccatg gtgctcgtgc     240
agatgcccat gtgcaatgag agagaggtgt accagcaatc catcggtgcg gtttgcagcc    300
tggactggcc aaggtcaaat tcctggtcc aggtgttgga tgactctgat gatgctacca     360
cttcggcact tatcaaggag gaggtggaga atggcagcg agagggtgtg cgcatagtat      420
accggcaccg ggtgatccgg gatggctaca aggctgaaaa cctgaaatca gccatgaact    480
gcagttacgt gaaagactat gagttcgttg tcatcttcga tgctgatttc aaccacagg     540 cggacttcct gaagcgcacc gtgccccatt tcaaggaaa ggatgacgtc gggttggttc      600
aggcgagatg gtcgttcgta acaaggatg agaacttgct gaccaggctt cagaacataa      660
atctttgctt ccacttcgag gtggagcagc aggtgaacgg ggcgtttctc aacttcttcg    720
ggttcaatgg caccgcggga gtctggagaa tcaaggcgct tgaggagtct ggaggatgga    780
tggagaggac gacggtggag gacatggaca tagctgttcg agcgcacctc aaagggtgga    840
agtttctctt tctaaacgat gtcgagtgtc agtgtgaatt gccagaatcg tatgaagcgt    900
acagaaagca gcagcaccgg tggcactcag gtcccatgca attgtttagg ctctgctttg    960
tggatataat caaatctaag atcggttcct ggaagaagtt caacctcata ttcctcttct   1020
tcctgctccg gaagctgata ctacccttct actccttcac cctcttctgc gtgatcctcc   1080
ccatgacgat gttcgtcccc gaagccgagc tccccgcgtg ggtggtgtgc acatcccgg     1140 cgacgatgtc catcctcaac atcctcccgt ccccgaaatc gttcccgttc atcgtcccgt    1200
acctgctgtt cgagaacacc atgtcggtga ccaagttcaa cgccatggtc tccggcctgt    1260
tccagctggg gagcgcctac gagtgggtcg tcaccaagaa gtcggggcgc tcctccgagg    1320
gcgacctcgt ggccctcgtg gagaagcact ccaagcagca gagggtaggc tcggcgccca    1380
acctcgacgc gctgaccaag gagtcgaagg gcaccgagga ggagaagaat aagaagaaga    1440
ggaagaagaa gcacaacagg atctacagga aggagctcgc gctgtccttc ctcctgctga    1500
ccgcggccgc ccgcagcttg ctgtccgccc agggcgtcca cttctacttc ctcctgttcc    1560
agggggtttc gttcttggtc gtcgggctcg acctgatcgg cgagcaggtg gattgatagc    1620
agttgaataa tgggttatat atatatatat atatatatat tttcgcttga agaaatcctc    1680
gcaggcatca tcaaattcaa agggctcttt gtgaagggaa gagcgtcgcc ttcttggatg    1740
cggaaacctt gggtccctgt tcctgttcca ggaggggtcg gaaacgtggg gagctgtgta    1800
gataggtata gcttggggtt tagcctgcga gatgcttttg ttcttccagg tttcgattct    1860
tttgtaagaa tatttgtgcc cctacatgca agggctctt                          1899
```

```
<210> SEQ ID NO 14
<211> LENGTH: 528
<212> TYPE: PRT
<213> ORGANISM: Zea mays

<400> SEQUENCE: 14
```

| | | | | | | | | | | | | | | |
|---|---|---|---|---|---|---|---|---|---|---|---|---|---|---|
| Met | Arg | Ala | Arg | Leu | Asp | Tyr | Leu | Ala | Pro | Pro | Leu | Gln | Phe | Leu | Thr |
| 1 | | | | 5 | | | | | 10 | | | | | 15 | |

Met Arg Ala Arg Leu Asp Tyr Leu Ala Pro Pro Leu Gln Phe Leu Thr
1               5                   10                  15

Asn Ala Cys Val Leu Leu Phe Leu Val Gln Ser Val Asp Arg Leu Val
            20                  25                  30

Leu Cys Leu Gly Cys Phe Trp Ile Lys Leu Lys Gly Val Arg Pro Val
        35                  40                  45

Pro Pro Leu Pro Ala Asp Lys Glu Asp Val Glu Ala Gly Pro Asp Gly
50                  55                  60

Val Pro Met Val Leu Val Gln Met Pro Met Cys Asn Glu Arg Glu Val
65                  70                  75                  80

Tyr Gln Gln Ser Ile Gly Ala Val Cys Ser Leu Asp Trp Pro Arg Ser
                85                  90                  95

Asn Phe Leu Val Gln Val Leu Asp Asp Ser Asp Asp Ala Thr Thr Ser
            100                 105                 110

Ala Leu Ile Lys Glu Glu Val Glu Lys Trp Gln Arg Glu Gly Val Arg
        115                 120                 125

Ile Val Tyr Arg His Arg Val Ile Arg Asp Gly Tyr Lys Ala Gly Asn
    130                 135                 140

Leu Lys Ser Ala Met Asn Cys Ser Tyr Val Lys Asp Tyr Glu Phe Val
145                 150                 155                 160

Val Ile Phe Asp Ala Asp Phe Gln Pro Gln Ala Asp Phe Leu Lys Arg
                165                 170                 175

Thr Val Pro His Phe Lys Gly Lys Asp Asp Val Gly Leu Val Gln Ala
            180                 185                 190

Arg Trp Ser Phe Val Asn Lys Asp Glu Asn Leu Leu Thr Arg Leu Gln
        195                 200                 205

Asn Ile Asn Leu Cys Phe His Phe Glu Val Glu Gln Gln Val Asn Gly
    210                 215                 220

Ala Phe Leu Asn Phe Phe Gly Phe Asn Gly Thr Ala Gly Val Trp Arg
225                 230                 235                 240

Ile Lys Ala Leu Glu Glu Ser Gly Gly Trp Met Glu Arg Thr Thr Val
                245                 250                 255

Glu Asp Met Asp Ile Ala Val Arg Ala His Leu Lys Gly Trp Lys Phe
            260                 265                 270

Leu Phe Leu Asn Asp Val Glu Cys Gln Cys Glu Leu Pro Glu Ser Tyr
        275                 280                 285

Glu Ala Tyr Arg Lys Gln Gln His Arg Trp His Ser Gly Pro Met Gln
    290                 295                 300

Leu Phe Arg Leu Cys Phe Val Asp Ile Ile Lys Ser Lys Ile Gly Phe
305                 310                 315                 320

Trp Lys Lys Phe Asn Leu Ile Phe Leu Phe Phe Leu Leu Arg Lys Leu
                325                 330                 335

Ile Leu Pro Phe Tyr Ser Phe Thr Leu Phe Cys Val Ile Leu Pro Met
            340                 345                 350

Thr Met Phe Val Pro Glu Ala Glu Leu Pro Ala Trp Val Val Cys Tyr
        355                 360                 365

Ile Pro Ala Thr Met Ser Ile Leu Asn Ile Leu Pro Ser Pro Lys Ser
    370                 375                 380

```
Phe Pro Phe Ile Val Pro Tyr Leu Leu Phe Glu Asn Thr Met Ser Val
385                 390                 395                 400

Thr Lys Phe Asn Ala Met Val Ser Gly Leu Phe Gln Leu Gly Ser Ala
            405                 410                 415

Tyr Glu Trp Val Val Thr Lys Lys Ser Gly Arg Ser Ser Glu Gly Asp
        420                 425                 430

Leu Val Ala Leu Val Glu Lys His Ser Lys Gln Gln Arg Val Gly Ser
    435                 440                 445

Ala Pro Asn Leu Asp Ala Leu Thr Lys Glu Ser Lys Gly Thr Glu Glu
450                 455                 460

Glu Lys Asn Lys Lys Arg Lys Lys Lys His Asn Arg Ile Tyr Arg
465                 470                 475                 480

Lys Glu Leu Ala Leu Ser Phe Leu Leu Leu Thr Ala Ala Ala Arg Ser
            485                 490                 495

Leu Leu Ser Ala Gln Gly Val His Phe Tyr Phe Leu Leu Phe Gln Gly
        500                 505                 510

Val Ser Phe Leu Val Val Gly Leu Asp Leu Ile Gly Glu Gln Val Asp
    515                 520                 525
```

<210> SEQ ID NO 15
<211> LENGTH: 1587
<212> TYPE: DNA
<213> ORGANISM: Zea mays

<400> SEQUENCE: 15

```
atgcgcgccc gcctcgacta cctcgcgccg ccgctgcagt tcctaaccaa cgcctgcgtc    60
ctcctcttcc tggtccagag cgtcgaccgc ctcgtgctct gcctcggctg cttctggatc   120
aagctcaagg gcgtcaggcc cgtgccgccg ctgcccgccg acaaggagga cgtcgaggcc   180
ggtcccgacg gcgtccccat ggtgctcgtg cagatgccca tgtgcaatga gagagaggtg   240
taccagcaat ccatcggtgc ggtttgcagc ctggactggc caaggtcaaa tttcctggtc   300
caggtgttgg atgactctga tgatgctacc acttcggcac ttatcaagga ggaggtggag   360
aaatggcagc gagagggtgt gcgcatagta taccggcacc gggtgatccg ggatggctac   420
aaggctggaa acctgaaatc agccatgaac tgcagttacg tgaaagacta tgagttcgtt   480
gtcatcttcg atgctgattt caaccacacg gcggacttcc tgaagcgcac cgtgccccat   540
ttcaagggaa aggatgacgt cgggttggtt caggcgagat ggtcgttcgt aaacaaggat   600
gagaacttgc tgaccaggct tcagaacata aatctttgct ccacttcga ggtggagcag   660
caggtgaacg ggcgtttct caacttcttc gggttcaatg caccgcggg agtctggaga   720
atcaaggcgc ttgaggagtc tggaggatgg atggagagga cgacggtgga ggacatggac   780
atagctgttc gagcgcacct caaagggtgg aagtttctct ttctaaacga tgtcgagtgt   840
cagtgtgaat tgccagaatc gtatgaagcg tacagaaagc agcagcaccg gtggcactca   900
ggtcccatgc aattgtttag ctctgctttt gtggatataa tcaaatctaa gatcggtttc   960
tggaagaagt tcaacctcat attcctcttc ttcctgctcc ggaagctgat actacccttc  1020
tactccttca ccctcttctg cgtgatcctc cccatgacga tgttcgtccc cgaagccgag  1080
ctccccgcgt gggtggtgtg ctacatcccg gcgacgatgt ccatcctcaa catcctcccg  1140
tccccgaaat cgttcccgtt catcgtcccg tacctgctgt tcgagaacac catgtcggtg  1200
accaagttca cgccatggt ctccggcctg ttccagctgg ggagcgccta cgagtgggtc  1260
gtcaccaaga gtcggggcg ctcctccgag ggcgacctcg tggccctcgt ggagaagcac  1320
```

```
tccaagcagc agagggtagg ctcggcgccc aacctcgacg cgctgaccaa ggagtcgaag      1380
ggcaccgagg aggagaagaa taagaagaag aggaagaaga agcacaacag gatctacagg      1440
aaggagctcg cgctgtcctt cctcctgctg accgcggccg cccgcagctt gctgtccgcc      1500
cagggcgtcc acttctactt cctcctgttc caggggtttt cgttcttggt cgtcgggctc      1560
gacctgatcg gcgagcaggt ggattga                                          1587
```

<210> SEQ ID NO 16
<211> LENGTH: 528
<212> TYPE: PRT
<213> ORGANISM: Zea mays

<400> SEQUENCE: 16

```
Met Arg Ala Arg Leu Asp Tyr Leu Ala Pro Leu Gln Phe Leu Thr
 1               5                  10                  15

Asn Ala Cys Val Leu Phe Leu Val Gln Ser Val Asp Arg Leu Val
             20                  25                  30

Leu Cys Leu Gly Cys Phe Trp Ile Lys Leu Lys Gly Val Arg Pro Val
         35                  40                  45

Pro Pro Leu Pro Ala Asp Lys Glu Asp Val Glu Ala Gly Pro Asp Gly
     50                  55                  60

Val Pro Met Val Leu Val Gln Met Pro Met Cys Asn Glu Arg Glu Val
 65                  70                  75                  80

Tyr Gln Gln Ser Ile Gly Ala Val Cys Ser Leu Asp Trp Pro Arg Ser
                 85                  90                  95

Asn Phe Leu Val Gln Val Leu Asp Asp Ser Asp Ala Thr Thr Ser
            100                 105                 110

Ala Leu Ile Lys Glu Glu Val Glu Lys Trp Gln Arg Glu Gly Val Arg
        115                 120                 125

Ile Val Tyr Arg His Arg Val Ile Arg Asp Gly Tyr Lys Ala Gly Asn
    130                 135                 140

Leu Lys Ser Ala Met Asn Cys Ser Tyr Val Lys Asp Tyr Glu Phe Val
145                 150                 155                 160

Val Ile Phe Asp Ala Asp Phe Gln Pro Gln Ala Asp Phe Leu Lys Arg
                165                 170                 175

Thr Val Pro His Phe Lys Gly Lys Asp Asp Val Gly Leu Val Gln Ala
            180                 185                 190

Arg Trp Ser Phe Val Asn Lys Asp Glu Asn Leu Leu Thr Arg Leu Gln
        195                 200                 205

Asn Ile Asn Leu Cys Phe His Phe Glu Val Glu Gln Gln Val Asn Gly
    210                 215                 220

Ala Phe Leu Asn Phe Phe Gly Phe Asn Gly Thr Ala Gly Val Trp Arg
225                 230                 235                 240

Ile Lys Ala Leu Glu Glu Ser Gly Gly Trp Met Glu Arg Thr Thr Val
                245                 250                 255

Glu Asp Met Asp Ile Ala Val Arg Ala His Leu Lys Gly Trp Lys Phe
            260                 265                 270

Leu Phe Leu Asn Asp Val Glu Cys Gln Cys Glu Leu Pro Glu Ser Tyr
        275                 280                 285

Glu Ala Tyr Arg Lys Gln Gln His Arg Trp His Ser Gly Pro Met Gln
    290                 295                 300

Leu Phe Arg Leu Cys Phe Val Asp Ile Ile Lys Ser Lys Ile Gly Phe
305                 310                 315                 320
```

```
Trp Lys Lys Phe Asn Leu Ile Phe Leu Phe Phe Leu Leu Arg Lys Leu
                325                 330                 335

Ile Leu Pro Phe Tyr Ser Phe Thr Leu Phe Cys Val Ile Leu Pro Met
            340                 345                 350

Thr Met Phe Val Pro Glu Ala Glu Leu Pro Ala Trp Val Val Cys Tyr
        355                 360                 365

Ile Pro Ala Thr Met Ser Ile Leu Asn Ile Leu Pro Ser Pro Lys Ser
    370                 375                 380

Phe Pro Phe Ile Val Pro Tyr Leu Leu Phe Glu Asn Thr Met Ser Val
385                 390                 395                 400

Thr Lys Phe Asn Ala Met Val Ser Gly Leu Phe Gln Leu Gly Ser Ala
                405                 410                 415

Tyr Glu Trp Val Val Thr Lys Lys Ser Gly Arg Ser Ser Glu Gly Asp
            420                 425                 430

Leu Val Ala Leu Val Glu Lys His Ser Lys Gln Gln Arg Val Gly Ser
        435                 440                 445

Ala Pro Asn Leu Asp Ala Leu Thr Lys Glu Ser Lys Gly Thr Glu Glu
    450                 455                 460

Glu Lys Asn Lys Lys Arg Lys Lys His Asn Arg Ile Tyr Arg
465                 470                 475                 480

Lys Glu Leu Ala Leu Ser Phe Leu Leu Leu Thr Ala Ala Arg Ser
                485                 490                 495

Leu Leu Ser Ala Gln Gly Val His Phe Tyr Phe Leu Leu Phe Gln Gly
            500                 505                 510

Val Ser Phe Leu Val Val Gly Leu Asp Leu Ile Gly Glu Gln Val Asp
        515                 520                 525

<210> SEQ ID NO 17
<211> LENGTH: 2551
<212> TYPE: DNA
<213> ORGANISM: Zea mays

<400> SEQUENCE: 17
cggacgcgtg ggtccggaga agaacctcc actggtcaca gcaaacacta tcctgtccat    60
ccttgctgct gactaccctg tggagaagct ttcttgctat gtttctgatg atggagggc    120 tctcctgact tttgaagcca tggctgaagc tgctagcttt gctaatatgt gggttccttt    180
ctgtcgcaag cacaacattg agcctcgcaa tcctgacagc tacttcaatc ttaagaagga    240
cccatacaag aacaaggttc gccaggattt tgtcaaggac aggaggaggg tcaagaggga    300
gtatgacgag ttcaaggtca ggatcaatgg tctgcctgac tcgatacgcc gacgctctga    360
tgcgtaccat gccagagagg aaatcaaggc tatgaagagg cagcgtgagg ccgctcttga    420
tgatgcagtg gagcctgtta agatccctaa agctacatgg atggctgatg cactcactg    480 gcctggtact tggattcaac cttctgctga gcatacccgt ggtgatcatg ctggaattat    540
tcaggtgatg ctgaaacctc ccagtgacga tcccttgtac ggcagcaccg tgatgaagg    600 cagacctctt gatttcaccg aggtcgacat ccgtttgcca atgctggtgt atgtgtcccg    660
agagaagcgg cctggttatg atcacaacaa gaaggctgga gcgatgaatg ctctggtccg    720
ttcatctgct gtcatgtcaa atggccctt catcctcaac ctcgactgtg atcactatgt    780
ctacaactcg caagctttcc gcgaagggat gtgcttcatg atggaccgtg gtggcgaccg    840
cattggttat gtccagttcc cgcagcggtt tgagggcatc gatccatcag atcgctatgc    900
caaccacaac accgtcttct tcgacgtcaa catgcgcgcg ctggatggtc tcatgggacc    960
```

```
agtctatgtt ggcactggct gccttttccg ccgtgttgcc ctatatggat ttgaccctcc    1020
gcgctccaag gagcacggtg gctgctgcag ctgttgcttc cccagagac gcaagatcaa    1080 agcttcagcc gctgcaccgg aggagacccg ggctctaagg atggcagact cgacgagga    1140 tgaaatgaac atgtcgtcgt tccccaagaa gtttggtaac tcgagcttcc tcatcgactc    1200
cattccgatt gctgagttcc aagggcgccc gcttgctgat caccctggtg tcaagaacgg    1260
ccgcccctcc ggtgctctca ctgtccccg tgaccttctg gatgcatcca cagtcgctga    1320
ggccgtcagt gtcatctcat gctggtacga agacaagacc gagtggggcc accgtgttgg    1380
ttggatctat ggctcggtga cggaggatgt ggtcactggg taccgatgc acaaccgggg    1440 ttggaagtcg gtgtactgtg tcaccaagcg tgacgccttc cgcggcaccg cgcccatcaa    1500
cctgaccgac cgtctccacc aggtgctccg gtgggctact ggatcagtgg agatcttctt    1560
ctcccgcaac aacgcgctgc tggcgagccg cagaatgaag ttcttgcaga ggatcgcgta    1620
cctgaacgtg gtatctaccc gttcacgtc catcttcctg atcgtctact gcttcctgcc    1680
ggcgctgtcg ctgttctcgg ggcagttcat cgtgaagacg ctgaacgtga cgttcctgac    1740
gtacctgctg gtgatcacgc tgacgctgtg cctgctggcg gtgctggaga tcaagtggtc    1800
ggggatcagc ctggaggagt ggtggcggaa cgagcagttc tggctgatcg gcggcacgag    1860
cgcgcacctg gcgccgtgc tgcagggcct gctgaaggtg gtggcgggca tcgagatctc    1920
cttcactctg acgtccaagt cgggcggcga cgacgtggac gacgagttcg cggacctgta    1980
catcgtcaag tggacgtcgc tgatgatccc gcccatcgtg atcatgatgg tgaacctgat    2040
cggcatcgcg gtcgggttca gccgcaccat ctacagcgag atcccgcagt ggagcaagct    2100
gctgggcggc gtcttcttca gcttctgggt gctggcgcac ctgtacccgt cgccaaggg    2160 cctgatgggg cggaggggcc gcacgccgac catcgtcttc gtctgggcgg gcctcctctc    2220
catcaccatc tcgctgctgt gggtggccat caacccgccg tcccagaacc agcagattgg    2280
tgggtcgttc acattcccct gaaagctctc tgggccaatg gcggattcat gcatgcttcg    2340
tcgcagtggg atccttgcgt tgctctgcat cagttcctgg ttgcagcggt tcactatctg    2400
aggacgaagc tgctgggggg aatgtgggat cctgactgtc gaactggcta cttttttgtt    2460
gtcgaagctg ataatactct tatgatgagc tatagtagta gttcttttgt tcttttgttt    2520
ttgctatata taaaatacat gttctggtcc c                                   2551
```

<210> SEQ ID NO 18
<211> LENGTH: 720
<212> TYPE: PRT
<213> ORGANISM: Zea mays

<400> SEQUENCE: 18

```
Met Ala Glu Ala Ala Ser Phe Ala Asn Met Trp Val Pro Phe Cys Arg
  1               5                  10                  15

Lys His Asn Ile Glu Pro Arg Asn Pro Asp Ser Tyr Phe Asn Leu Lys
                 20                  25                  30

Lys Asp Pro Tyr Lys Asn Lys Val Arg Gln Asp Phe Val Lys Asp Arg
             35                  40                  45

Arg Arg Val Lys Arg Glu Tyr Asp Glu Phe Lys Val Arg Ile Asn Gly
         50                  55                  60

Leu Pro Asp Ser Ile Arg Arg Ser Asp Ala Tyr His Ala Arg Glu
 65                  70                  75                  80

Glu Ile Lys Ala Met Lys Arg Gln Arg Glu Ala Ala Leu Asp Asp Ala
                 85                  90                  95
```

-continued

```
Val Glu Pro Val Lys Ile Pro Lys Ala Thr Trp Met Ala Asp Gly Thr
            100                 105                 110

His Trp Pro Gly Thr Trp Ile Gln Pro Ser Ala Glu His Thr Arg Gly
        115                 120                 125

Asp His Ala Gly Ile Ile Gln Val Met Leu Lys Pro Pro Ser Asp Asp
    130                 135                 140

Pro Leu Tyr Gly Ser Thr Gly Asp Glu Gly Arg Pro Leu Asp Phe Thr
145                 150                 155                 160

Glu Val Asp Ile Arg Leu Pro Met Leu Val Tyr Val Ser Arg Glu Lys
                165                 170                 175

Arg Pro Gly Tyr Asp His Asn Lys Lys Ala Gly Ala Met Asn Ala Leu
            180                 185                 190

Val Arg Ser Ser Ala Val Met Ser Asn Gly Pro Phe Ile Leu Asn Leu
        195                 200                 205

Asp Cys Asp His Tyr Val Tyr Asn Ser Gln Ala Phe Arg Glu Gly Met
    210                 215                 220

Cys Phe Met Met Asp Arg Gly Gly Asp Arg Ile Gly Tyr Val Gln Phe
225                 230                 235                 240

Pro Gln Arg Phe Glu Gly Ile Asp Pro Ser Arg Tyr Ala Asn His
                245                 250                 255

Asn Thr Val Phe Phe Asp Val Asn Met Arg Ala Leu Asp Gly Leu Met
            260                 265                 270

Gly Pro Val Tyr Val Gly Thr Gly Cys Leu Phe Arg Arg Val Ala Leu
        275                 280                 285

Tyr Gly Phe Asp Pro Pro Arg Ser Lys Glu His Gly Gly Cys Cys Ser
    290                 295                 300

Cys Cys Phe Pro Gln Arg Arg Lys Ile Lys Ala Ser Ala Ala Ala Pro
305                 310                 315                 320

Glu Glu Thr Arg Ala Leu Arg Met Ala Asp Phe Asp Glu Asp Glu Met
                325                 330                 335

Asn Met Ser Ser Phe Pro Lys Lys Phe Gly Asn Ser Ser Phe Leu Ile
            340                 345                 350

Asp Ser Ile Pro Ile Ala Glu Phe Gln Gly Arg Pro Leu Ala Asp His
        355                 360                 365

Pro Gly Val Lys Asn Gly Arg Pro Pro Gly Ala Leu Thr Val Pro Arg
    370                 375                 380

Asp Leu Leu Asp Ala Ser Thr Val Ala Glu Ala Val Ser Val Ile Ser
385                 390                 395                 400

Cys Trp Tyr Glu Asp Lys Thr Glu Trp Gly His Arg Val Gly Trp Ile
                405                 410                 415

Tyr Gly Ser Val Thr Glu Asp Val Val Thr Gly Tyr Arg Met His Asn
            420                 425                 430

Arg Gly Trp Lys Ser Val Tyr Cys Val Thr Lys Arg Asp Ala Phe Arg
        435                 440                 445

Gly Thr Ala Pro Ile Asn Leu Thr Asp Arg Leu His Gln Val Leu Arg
    450                 455                 460

Trp Ala Thr Gly Ser Val Glu Ile Phe Phe Ser Arg Asn Asn Ala Leu
465                 470                 475                 480

Leu Ala Ser Arg Arg Met Lys Phe Leu Gln Arg Ile Ala Tyr Leu Asn
                485                 490                 495

Val Gly Ile Tyr Pro Phe Thr Ser Ile Phe Leu Ile Val Tyr Cys Phe
            500                 505                 510
```

| | | | | | | | | | | | |
|---|---|---|---|---|---|---|---|---|---|---|---|
Leu Pro Ala Leu Ser Leu Phe Ser Gly Gln Phe Ile Val Lys Thr Leu
        515                    520                    525

Asn Val Thr Phe Leu Thr Tyr Leu Leu Val Ile Thr Leu Thr Leu Cys
530                 535                 540

Leu Leu Ala Val Leu Glu Ile Lys Trp Ser Gly Ile Ser Leu Glu Glu
545                 550                 555                 560

Trp Trp Arg Asn Glu Gln Phe Trp Leu Ile Gly Gly Thr Ser Ala His
                565                 570                 575

Leu Ala Ala Val Leu Gln Gly Leu Leu Lys Val Val Ala Gly Ile Glu
                580                 585                 590

Ile Ser Phe Thr Leu Thr Ser Lys Ser Gly Asp Asp Val Asp Asp
                595                 600                 605

Glu Phe Ala Asp Leu Tyr Ile Val Lys Trp Thr Ser Leu Met Ile Pro
610                 615                 620

Pro Ile Val Ile Met Met Val Asn Leu Ile Gly Ile Ala Val Gly Phe
625                 630                 635                 640

Ser Arg Thr Ile Tyr Ser Glu Ile Pro Gln Trp Ser Lys Leu Leu Gly
                645                 650                 655

Gly Val Phe Phe Ser Phe Trp Val Leu Ala His Leu Tyr Pro Phe Ala
                660                 665                 670

Lys Gly Leu Met Gly Arg Arg Gly Arg Thr Pro Thr Ile Val Phe Val
                675                 680                 685

Trp Ala Gly Leu Leu Ser Ile Thr Ile Ser Leu Leu Trp Val Ala Ile
                690                 695                 700

Asn Pro Pro Ser Gln Asn Gln Gln Ile Gly Gly Ser Phe Thr Phe Pro
705                 710                 715                 720

```
<210> SEQ ID NO 19
<211> LENGTH: 1740
<212> TYPE: DNA
<213> ORGANISM: Zea mays

<400> SEQUENCE: 19
gagcagtgcc tgaacccaag tgcagtgcag cagccatggg agcagcagca gcaggtggcc        60
acgcgctgcg cgccgtcggc gacgtcgtct cgttccccgc gaccgtcgcc gccttcgtgg       120
aggcgctgct ccagggctgg gccgaggcca gggccgggct gctggtgccg ctgctccgcg       180
ccgcggtgct gctgtgcacg gccatgtcgc tgatcgtgct ggccgagaag gtgttcctgg       240
gcgcggtcag ctccgtggcg aagctgcggg ccggcgtccg gggcgggtg tgcaggtgcg       300 accccgacga ggaggcggct gcggcatccc aggcctatcc catggtgctc gtccagatcc       360
ccatgtacaa cgagagggag gtttaccagc tatcaataga ggcagcctgc aggctcacat       420
ggccggtaga tcgactaata gtgcaggtgc tggacgactc caccgactcc gtcatcaagg       480
agctggtgaa gggcgagtgc gagcggtggg ccacggagga ggggatcaac gtcaagtacg       540
agacgcgcaa ggacagggcc gggtacaagg ccggcaacct caaggagggg atgcgccacg       600
cctacgtgcg cgcctgcgag ttcgtcgcca tgttcgacgc agacttccag ccgccgccgg       660
acttcctcgt cagaaccgtc ccgttcctcg tccacaaccc cagcctcgcg ctcgtgcaga       720
cacgctggaa gttcgtgaat gccaacgact gcttgctgac gagaatgcag gagatgtcca       780
tggactacca tttcaaggtg gagcaggaag ctggctcttc cttatgcaac ttcttttggat       840 acaacggaac cgctggagta tgagaacgc aagcgatcgt cgagtccggg ggctggagg       900 accgaaccac tgctgaggac atggacttgg cgctgagagc agggctcctg gctgggagt       960
```

-continued

```
tcgtctacgt tggaagcata aaggttaaga gtgagctgcc gagcactctc aaggcgtacc   1020
ggtcccagca gcaccgctgg tcatgcggac ctgcctcct gttcaagaaa atgttctggc    1080
aaattctcgc tgccgagaga gtgtcggtct ggaagaagtg gtacatggtc tatgacttct   1140
tcattgcccg gagaatcgta ggcaccttct acacgttctt ctttttcagc gtcctgattc   1200
ctctgaacat tctgctaccc gaagcgcaga ttcctgtgtg ggagctcatc tatatcccca   1260
tagctatcac tcttctcaac tctgttggga ctccaaggtc tatccatctg gtcatactgt   1320
gggtcttgtt cgagaacgta atggcgttgc atcggtttaa agccatcttg atagggtttc   1380
tcgaagctga cagggccaac gaatggatcg tgacgcaaaa gctggggaat ctgcagaagc   1440
tgaaatcgat cgccagactt acaggaagct accgtttcaa agacaggttc catttcctgg   1500
aggtgttcat tgggctgttc cttttggcct ctgcgtgctt tgactactta tacagagatg   1560
actatgttta cctctttgtt cttccccaat cgatcatgta tttcgcgatt gggtttcagt   1620
tcgttggtct caatgtctct gaagactgac caattgcaag acaactgaac gttttggttg   1680
cgatattatg attgctcggg tcaaggttct tgtaaaaaaa aaaaaaaaaa aaaaaaaaa    1740
```

<210> SEQ ID NO 20
<211> LENGTH: 537
<212> TYPE: PRT
<213> ORGANISM: Zea mays

<400> SEQUENCE: 20

```
Met Gly Ala Ala Ala Gly Gly His Ala Leu Arg Ala Val Gly Asp
  1               5                  10                  15

Val Val Ser Phe Pro Ala Thr Val Ala Ala Phe Val Glu Ala Leu Leu
                 20                  25                  30

Gln Gly Trp Ala Glu Ala Arg Ala Gly Leu Leu Val Pro Leu Leu Arg
             35                  40                  45

Ala Ala Val Leu Leu Cys Thr Ala Met Ser Leu Ile Val Leu Ala Glu
         50                  55                  60

Lys Val Phe Leu Gly Ala Val Ser Ser Val Ala Lys Leu Arg Arg Arg
 65                  70                  75                  80

Arg Pro Gly Arg Val Cys Arg Cys Asp Pro Asp Glu Glu Ala Ala Ala
                 85                  90                  95

Ala Ser Gln Ala Tyr Pro Met Val Leu Val Gln Ile Pro Met Tyr Asn
                100                 105                 110

Glu Arg Glu Val Tyr Gln Leu Ser Ile Glu Ala Ala Cys Arg Leu Thr
            115                 120                 125

Trp Pro Val Asp Arg Leu Ile Val Gln Val Leu Asp Asp Ser Thr Asp
        130                 135                 140

Ser Val Ile Lys Glu Leu Val Lys Gly Glu Cys Glu Arg Trp Ala Thr
145                 150                 155                 160

Glu Glu Gly Ile Asn Val Lys Tyr Glu Thr Arg Lys Asp Arg Ala Gly
                165                 170                 175

Tyr Lys Ala Gly Asn Leu Lys Glu Gly Met Arg His Ala Tyr Val Arg
            180                 185                 190

Ala Cys Glu Phe Val Ala Met Phe Asp Ala Asp Phe Gln Pro Pro Pro
        195                 200                 205

Asp Phe Leu Val Arg Thr Val Pro Phe Leu Val His Asn Pro Ser Leu
    210                 215                 220

Ala Leu Val Gln Thr Arg Trp Lys Phe Val Asn Ala Asn Asp Cys Leu
225                 230                 235                 240
```

```
Leu Thr Arg Met Gln Glu Met Ser Met Asp Tyr His Phe Lys Val Glu
            245                 250                 255

Gln Glu Ala Gly Ser Ser Leu Cys Asn Phe Phe Gly Tyr Asn Gly Thr
        260                 265                 270

Ala Gly Val Trp Arg Thr Gln Ala Ile Val Glu Ser Gly Gly Trp Glu
    275                 280                 285

Asp Arg Thr Thr Ala Glu Asp Met Asp Leu Ala Leu Arg Ala Gly Leu
290                 295                 300

Leu Gly Trp Glu Phe Val Tyr Val Gly Ser Ile Lys Val Lys Ser Glu
305                 310                 315                 320

Leu Pro Ser Thr Leu Lys Ala Tyr Arg Ser Gln His Arg Trp Ser
            325                 330                 335

Cys Gly Pro Ala Leu Leu Phe Lys Lys Met Phe Trp Gln Ile Leu Ala
            340                 345                 350

Ala Glu Arg Val Ser Val Trp Lys Lys Trp Tyr Met Val Tyr Asp Phe
        355                 360                 365

Phe Ile Ala Arg Arg Ile Val Gly Thr Phe Tyr Thr Phe Phe Phe
    370                 375                 380

Ser Val Leu Ile Pro Leu Asn Ile Leu Pro Glu Ala Gln Ile Pro
385                 390                 395                 400

Val Trp Glu Leu Ile Tyr Ile Pro Ile Ala Ile Thr Leu Leu Asn Ser
            405                 410                 415

Val Gly Thr Pro Arg Ser Ile His Leu Val Ile Leu Trp Val Leu Phe
            420                 425                 430

Glu Asn Val Met Ala Leu His Arg Phe Lys Ala Ile Leu Ile Gly Phe
        435                 440                 445

Leu Glu Ala Asp Arg Ala Asn Glu Trp Ile Val Thr Gln Lys Leu Gly
    450                 455                 460

Asn Leu Gln Lys Leu Lys Ser Ile Ala Arg Leu Thr Gly Ser Tyr Arg
465                 470                 475                 480

Phe Lys Asp Arg Phe His Phe Leu Glu Val Phe Ile Gly Leu Phe Leu
            485                 490                 495

Leu Ala Ser Ala Cys Phe Asp Tyr Leu Tyr Arg Asp Asp Tyr Val Tyr
            500                 505                 510

Leu Phe Val Leu Pro Gln Ser Ile Met Tyr Phe Ala Ile Gly Phe Gln
        515                 520                 525

Phe Val Gly Leu Asn Val Ser Glu Asp
    530                 535

<210> SEQ ID NO 21
<211> LENGTH: 1834
<212> TYPE: DNA
<213> ORGANISM: Zea mays

<400> SEQUENCE: 21
aaccaccaca ccaccaccca atggaggccg gggaaatcgg cggggcccctt gtcttcatcc      60 tcgccgccgc cgccgccgtc gcggccgccg tgtccgtcgg cgcggtcgac ttcagccgcc     120
cgctcaccgc gggggcgccg ttcgacttcc aggcggcggt gtcctggctc atcggcatcc     180
tcgacggcac gtcctcggca gcggcggacg tggacggggc gtgggtggcg gtgcgggccg     240
gggtgatcgc gccggtgctg caggtggcgg tgtgggcgtg catggtgatg tcggtgatgc     300
tggtggtgga ggccgtgtac aacagcgtca tcagcctcgg cgtcaaggcc attgggtgga     360
ggcctgagtg gaggttcaag tggaagcccc tcgacagcgc cgacgaggag aaggggaccg     420
```

```
cccacttccc tatggtcctg gttcagatac ccatgtacaa cgagctggag gtgtacaagc    480
tgtcaatagc ggcagcatgt gagctgcagt ggccaaagga caggatagta attcaagtgt    540
tggacgattc tactgacccc tttatcaaga atttggtgga gcttgaatgt gagcactggg    600
tgaacaaagg tgtcaatatt aagtatgcca caagaaccag ccgcaaggga ttcaaggcag    660
gagctctgaa gaaaggaatg gaatgtgact atgcatggca aagcgaatac attgctatat    720
ttgatgctga tttccaacct gaaccagatt ttctgctcca aactgtccca ttccttctgc    780
acaatccaga agttgcactt gttcaagctc ggtggtcctt cgtgaatgac acgacaagcc    840
tgctgacaag ggtacaaaag atgttttacg actaccactt caaagttgaa caagaagcag    900
gatcagcgac ctttgccttc ttcagtttca cggaactgc tggagtgtgg cgtacaggag     960
ccataagaga tgcaggaggt tggaaggacc gaactacagt tgaagacatg gacttggcgg   1020
ttcgagcaac actaaagggc tggaaattcg tatatgttgg agacgttaga gtcaagagtg   1080
aactgccgtc cacttacaag gcctgtcggc agcaattccg gtggtctagt ggtggtgcaa   1140
acttattccg taagatggca aaggatgttt tgtttgccaa ggatatatca ctcgtcaaga   1200
agttctatat gctctatagc ttcttctttg tgaggagagt tgtagcgccg acggctgcct   1260
gtattctcta caatgtcatc atccccatct cagtcacaat cccggagctt acctaccag    1320
tgtggggtgt tgcctatatt cccatggtgc ttaccgtggt cacagctata agacatccaa   1380
aaaatctaca catactgcca ttttggattt tgtttgagag tgtgatgaca ttgcatcgga   1440
tgagggctgc gatgactgga ctgctggagc tagaaggatt caaccagtgg attgtgacaa   1500
agaaggtggg gaatgatctc gaggacactg aagttccttt gcttcagaaa acccggaaaa   1560
ggctgagaga cagagtcaat ctcccccgaga ttggattttc ggtgtttctc ttcctctgtg   1620
catcatacaa cctggtgttc catgggaaaa caagctacta cttatatatg taccttcagg   1680
ggttagcatt tctgttacta gggtttaact tcactggcaa ttgttcttgc taccaatgat   1740
agcatgtcaa agctgtacga attgctgatt gatattcatt ttctggtcat gcgttcgtaa   1800
aaaaaaaaaa aaaaaaaaaa aaaaaaaaaa aaaa                               1834
```

<210> SEQ ID NO 22
<211> LENGTH: 572
<212> TYPE: PRT
<213> ORGANISM: Zea mays

<400> SEQUENCE: 22

```
Met Glu Ala Gly Glu Ile Gly Gly Ala Leu Val Phe Ile Leu Ala Ala
 1               5                  10                  15

Ala Ala Val Ala Ala Ala Val Ser Val Gly Ala Val Asp Phe Ser
            20                  25                  30

Arg Pro Leu Thr Ala Gly Ala Pro Phe Asp Phe Gln Ala Ala Val Ser
        35                  40                  45

Trp Leu Ile Gly Ile Leu Asp Gly Thr Ser Ser Ala Ala Ala Asp Val
    50                  55                  60

Asp Gly Ala Trp Val Ala Val Arg Ala Gly Val Ile Ala Pro Val Leu
65                  70                  75                  80

Gln Val Ala Val Trp Ala Cys Met Val Met Ser Val Met Leu Val Val
                85                  90                  95

Glu Ala Val Tyr Asn Ser Val Ile Ser Leu Gly Val Lys Ala Ile Gly
            100                 105                 110

Trp Arg Pro Glu Trp Arg Phe Lys Trp Lys Pro Leu Asp Ser Ala Asp
        115                 120                 125
```

```
Glu Glu Lys Gly Thr Ala His Phe Pro Met Val Leu Val Gln Ile Pro
            130                 135                 140
Met Tyr Asn Glu Leu Glu Val Tyr Lys Leu Ser Ile Ala Ala Ala Cys
145                 150                 155                 160
Glu Leu Gln Trp Pro Lys Asp Arg Ile Val Ile Gln Val Leu Asp Asp
                165                 170                 175
Ser Thr Asp Pro Phe Ile Lys Asn Leu Val Glu Leu Glu Cys Glu His
            180                 185                 190
Trp Val Asn Lys Gly Val Asn Ile Lys Tyr Ala Thr Arg Thr Ser Arg
        195                 200                 205
Lys Gly Phe Lys Ala Gly Ala Leu Lys Lys Gly Met Glu Cys Asp Tyr
210                 215                 220
Ala Trp Gln Ser Glu Tyr Ile Ala Ile Phe Asp Ala Asp Phe Gln Pro
225                 230                 235                 240
Glu Pro Asp Phe Leu Leu Gln Thr Val Pro Phe Leu Leu His Asn Pro
                245                 250                 255
Glu Val Ala Leu Val Gln Ala Arg Trp Ser Phe Val Asn Asp Thr Thr
            260                 265                 270
Ser Leu Leu Thr Arg Val Gln Lys Met Phe Tyr Asp Tyr His Phe Lys
        275                 280                 285
Val Glu Gln Glu Ala Gly Ser Ala Thr Phe Ala Phe Phe Ser Phe Asn
    290                 295                 300
Gly Thr Ala Gly Val Trp Arg Thr Gly Ala Ile Arg Asp Ala Gly Gly
305                 310                 315                 320
Trp Lys Asp Arg Thr Thr Val Glu Asp Met Asp Leu Ala Val Arg Ala
                325                 330                 335
Thr Leu Lys Gly Trp Lys Phe Val Tyr Val Gly Asp Val Arg Val Lys
            340                 345                 350
Ser Glu Leu Pro Ser Thr Tyr Lys Ala Cys Arg Gln Gln Phe Arg Trp
        355                 360                 365
Ser Ser Gly Gly Ala Asn Leu Phe Arg Lys Met Ala Lys Asp Val Leu
    370                 375                 380
Phe Ala Lys Asp Ile Ser Leu Val Lys Lys Phe Tyr Met Leu Tyr Ser
385                 390                 395                 400
Phe Phe Phe Val Arg Arg Val Val Ala Pro Thr Ala Ala Cys Ile Leu
                405                 410                 415
Tyr Asn Val Ile Ile Pro Ile Ser Val Thr Ile Pro Glu Leu Tyr Leu
            420                 425                 430
Pro Val Trp Gly Val Ala Tyr Ile Pro Met Val Leu Thr Val Val Thr
        435                 440                 445
Ala Ile Arg His Pro Lys Asn Leu His Ile Leu Pro Phe Trp Ile Leu
    450                 455                 460
Phe Glu Ser Val Met Thr Leu His Arg Met Arg Ala Ala Met Thr Gly
465                 470                 475                 480
Leu Leu Glu Leu Glu Gly Phe Asn Gln Trp Ile Val Thr Lys Lys Val
                485                 490                 495
Gly Asn Asp Leu Glu Asp Thr Gly Val Pro Leu Leu Gln Lys Thr Arg
            500                 505                 510
Lys Arg Leu Arg Asp Arg Val Asn Leu Pro Glu Ile Gly Phe Ser Val
        515                 520                 525
Phe Leu Phe Leu Cys Ala Ser Tyr Asn Leu Val Phe His Gly Lys Thr
    530                 535                 540
```

```
Ser Tyr Tyr Leu Tyr Met Tyr Leu Gln Gly Leu Ala Phe Leu Leu Leu
545                 550                 555                 560

Gly Phe Asn Phe Thr Gly Asn Cys Ser Cys Tyr Gln
            565                 570

<210> SEQ ID NO 23
<211> LENGTH: 2432
<212> TYPE: DNA
<213> ORGANISM: Zea mays

<400> SEQUENCE: 23
ccacgcgtcc gccggtcctc ggctcatcag tattattatt attattatta ttcggctcct      60
gctcatcagc tgcagcagtc gtgctccgga ccggagaagt cgaaatggag gagaggctgt     120
tcgccacgga gaagcacggt ggccgggcgc tctacaggct ccacgccgtc acggtgttcc     180
tggggatatg cctgctgctc tgctacaggg cgacgcacgt cccggctgcc ggctccggcg     240
gcagggcggc gtggctgggg atgctcgcgg cggagctctg gttcggcttc tactgggtca     300
tcacgcagtc cgtgcgctgg tgccccatcc gccgccgcac cttccacgac aggctcgccg     360
ccaggttcgg agagcggctc ccctgcgtgg acatcttcgt gtgcacagcg gacccgcggt     420
cggagccgcc gagccttgtc gtggccacgg tcctgtcggt gatggcgtac aactacccgc     480
ccgcgaagct caacgtctac ctctccgacg acggcggctc catcctcacc ttctacgctc     540
tgtgggaggc ctccgccttc gccaagcact ggctcccgtt ctgcaggagg tacggcgtcg     600
agccacggtc gccggccgct tacttcgccc agtctgatga aagcctcgt catgatccgc      660 cgcacgcctt gcaggagtgg acgtccgtca aaaacctata cgatgaaatg acggagcgga     720
ttgactccgc tgctcggacg ggcaatgttc ctgaagaaac tagagcgaaa cacaaagggt     780
tttctgagtg ggatacgggt attacctcaa aagaccacca cccgatcgtt cagattctga     840
tagatgggaa agacaaggct gtagctgaca acgaaggcaa tgtgctgccg acgctggtgt     900
acgtggcacg agagaagagg cctcagtacc accacaactt caaagccggg gcgatgaacg     960
ctctgatccg agtatcgtcc gtgataagca acagccctat catcctgaac gtggactgcg    1020
acatgtattc caacaacagc gacacgatca gagacgcgct gtgcttcttc ctcgacgaag    1080
aaacgggcca caggatcgcg ttcgtgcagt accctcagaa ctacaacaac ctcaccaaga    1140
acaacatata cggcaactcc ctcaatgtca tcaaccaggt ggagctgagc ggcctggacg    1200 cttgggcgg cccgctgtac atcggcacgg gatgcttcca taggaggag acccctgtgcg     1260 gcaggaggtt caccgaggac tacaaggaag actgggacag aggaaccaag gagcagcagc    1320
agcaccgcca ccgcgtcgac ggcgagaccg aagcgaaggc caagtcgcta gcgacctgcg    1380
cctacgagca cgacgacgac acgcggtggg gagacgaggt ggggctcaag tacggctgct    1440
cggtggagga cgtcatcacg gggctggcga tacactgcag agggtgggag tcggtgtaca    1500
gcaaccccgc gagagcggcg ttcgtcggcg tcgcgccgac cacgctcgcc cagaccatac    1560
tgcagcacaa gcggtggagc gagggcaact tcggcatctt cgtttccagg tactgcccct    1620 tcgtcttgg acgacgggc aaaaccaggt tgccgcacca gatgggctac tccatctacg      1680 gctatgggc gcccaactcg ctgcctacgc tgtactacgc tgtcgtccct tcgctgtgcc    1740
tgctcaaggg caccccctg ttccctgagc tcacgagtcc gtggatcgcg cctttcgtct    1800
acgtcgcggt cgccaagaac gtctacagcg cgtgggaggc gctgtggtgc ggagacacgc    1860
tgagagggtg gtgaacggg cagaggatgt ggctggtccg gagaacgacc tcgtacctct    1920
acggcttcgt cgacaccgtc agggactcgc tggggctgtc caagatgggc ttcgtggtgt    1980
```

```
cgtccaaggt gagcgacgag gacgaggcca agaggtacga gcaggagatg atggagttcg   2040
ggacggcgtc gccggagtac gtgatcgtcg cggccgtcgc gctgctcaac ctcgtgtgcc   2100
tggcagggat ggcggcggca ctggatgtgt tcttcgtcca ggtcgctctc tgcggggtgc   2160
tggtgctcct caacgtcccg gtctatgaag ccatgttcgt caggaaggac agggggagga   2220
tgccgttccc gatcacgcta gcctccgttg gctttgtgac gctggccctc attgtgccat   2280
tcttttgact ttgaggtgct aataatacgt gtacgggcac acgcacgttc gcatgtatga   2340
cgattatggg caacaggcgt gtaataccac taatacctat taaacactcc agtctccaag   2400
tgatccattg ctacaaaaaa aaaaaaaaaa aa                                 2432
```

<210> SEQ ID NO 24
<211> LENGTH: 727
<212> TYPE: PRT
<213> ORGANISM: Zea mays

<400> SEQUENCE: 24

```
Met Glu Glu Arg Leu Phe Ala Thr Glu Lys His Gly Gly Arg Ala Leu
 1               5                  10                  15

Tyr Arg Leu His Ala Val Thr Val Phe Leu Gly Ile Cys Leu Leu Leu
            20                  25                  30

Cys Tyr Arg Ala Thr His Val Pro Ala Ala Gly Ser Gly Gly Arg Ala
        35                  40                  45

Ala Trp Leu Gly Met Leu Ala Ala Glu Leu Trp Phe Gly Phe Tyr Trp
    50                  55                  60

Val Ile Thr Gln Ser Val Arg Trp Cys Pro Ile Arg Arg Arg Thr Phe
65                  70                  75                  80

His Asp Arg Leu Ala Ala Arg Phe Gly Glu Arg Leu Pro Cys Val Asp
                85                  90                  95

Ile Phe Val Cys Thr Ala Asp Pro Arg Ser Glu Pro Pro Ser Leu Val
            100                 105                 110

Val Ala Thr Val Leu Ser Val Met Ala Tyr Asn Tyr Pro Pro Ala Lys
        115                 120                 125

Leu Asn Val Tyr Leu Ser Asp Asp Gly Gly Ser Ile Leu Thr Phe Tyr
    130                 135                 140

Ala Leu Trp Glu Ala Ser Ala Phe Ala Lys His Trp Leu Pro Phe Cys
145                 150                 155                 160

Arg Arg Tyr Gly Val Glu Pro Arg Ser Pro Ala Ala Tyr Phe Ala Gln
                165                 170                 175

Ser Asp Glu Lys Pro Arg His Asp Pro Pro His Ala Leu Gln Glu Trp
            180                 185                 190

Thr Ser Val Lys Asn Leu Tyr Asp Glu Met Thr Glu Arg Ile Asp Ser
        195                 200                 205

Ala Ala Arg Thr Gly Asn Val Pro Glu Glu Thr Arg Ala Lys His Lys
    210                 215                 220

Gly Phe Ser Glu Trp Asp Thr Gly Ile Thr Ser Lys Asp His His Pro
225                 230                 235                 240

Ile Val Gln Ile Leu Ile Asp Gly Lys Asp Lys Ala Val Ala Asp Asn
                245                 250                 255

Glu Gly Asn Val Leu Pro Thr Leu Val Tyr Val Ala Arg Glu Lys Arg
            260                 265                 270

Pro Gln Tyr His His Asn Phe Lys Ala Gly Ala Met Asn Ala Leu Ile
        275                 280                 285
```

-continued

```
Arg Val Ser Ser Val Ile Ser Asn Ser Pro Ile Ile Leu Asn Val Asp
    290                 295                 300

Cys Asp Met Tyr Ser Asn Asn Ser Asp Thr Ile Arg Asp Ala Leu Cys
305                 310                 315                 320

Phe Phe Leu Asp Glu Glu Thr Gly His Arg Ile Ala Phe Val Gln Tyr
                325                 330                 335

Pro Gln Asn Tyr Asn Asn Leu Thr Lys Asn Asn Ile Tyr Gly Asn Ser
            340                 345                 350

Leu Asn Val Ile Asn Gln Val Glu Leu Ser Gly Leu Asp Ala Trp Gly
                355                 360                 365

Gly Pro Leu Tyr Ile Gly Thr Gly Cys Phe His Arg Arg Glu Thr Leu
    370                 375                 380

Cys Gly Arg Arg Phe Thr Glu Asp Tyr Lys Glu Asp Trp Asp Arg Gly
385                 390                 395                 400

Thr Lys Glu Gln Gln Gln His Arg His Arg Val Asp Gly Glu Thr Glu
                405                 410                 415

Ala Lys Ala Lys Ser Leu Ala Thr Cys Ala Tyr Glu His Asp Asp Asp
            420                 425                 430

Thr Arg Trp Gly Asp Glu Val Gly Leu Lys Tyr Gly Cys Ser Val Glu
    435                 440                 445

Asp Val Ile Thr Gly Leu Ala Ile His Cys Arg Gly Trp Glu Ser Val
450                 455                 460

Tyr Ser Asn Pro Ala Arg Ala Ala Phe Val Gly Val Ala Pro Thr Thr
465                 470                 475                 480

Leu Ala Gln Thr Ile Leu Gln His Lys Arg Trp Ser Glu Gly Asn Phe
                485                 490                 495

Gly Ile Phe Val Ser Arg Tyr Cys Pro Phe Val Phe Gly Arg Arg Gly
            500                 505                 510

Lys Thr Arg Leu Pro His Gln Met Gly Tyr Ser Ile Tyr Gly Leu Trp
    515                 520                 525

Ala Pro Asn Ser Leu Pro Thr Leu Tyr Tyr Ala Val Val Pro Ser Leu
530                 535                 540

Cys Leu Leu Lys Gly Thr Pro Leu Phe Pro Glu Leu Thr Ser Pro Trp
545                 550                 555                 560

Ile Ala Pro Phe Val Tyr Val Ala Val Ala Lys Asn Val Tyr Ser Ala
                565                 570                 575

Trp Glu Ala Leu Trp Cys Gly Asp Thr Leu Arg Gly Trp Trp Asn Gly
            580                 585                 590

Gln Arg Met Trp Leu Val Arg Thr Thr Ser Tyr Leu Tyr Gly Phe
    595                 600                 605

Val Asp Thr Val Arg Asp Ser Leu Gly Leu Ser Lys Met Gly Phe Val
610                 615                 620

Val Ser Ser Lys Val Ser Asp Glu Asp Glu Ala Lys Arg Tyr Glu Gln
625                 630                 635                 640

Glu Met Met Glu Phe Gly Thr Ala Ser Pro Glu Tyr Val Ile Val Ala
                645                 650                 655

Ala Val Ala Leu Leu Asn Leu Val Cys Leu Ala Gly Met Ala Ala Ala
            660                 665                 670

Leu Asp Val Phe Phe Val Gln Val Ala Leu Cys Gly Val Leu Val Leu
    675                 680                 685

Leu Asn Val Pro Val Tyr Glu Ala Met Phe Val Arg Lys Asp Arg Gly
690                 695                 700
```

```
Arg Met Pro Phe Pro Ile Thr Leu Ala Ser Val Gly Phe Val Thr Leu
705                 710                 715                 720

Ala Leu Ile Val Pro Phe Phe
                725
```

<210> SEQ ID NO 25
<211> LENGTH: 1190
<212> TYPE: DNA
<213> ORGANISM: Zea mays

<400> SEQUENCE: 25

```
gcacgagcac acgcacgcat acacagcaca gagtgaggta agcatccgaa aaaagctgtg        60
atctgatcga catggccgcc gccaccatgg ctctcacctc ccgcgcgctc gtcggcaagc       120
cggcgaccag caccagggac gtcttcggcg aggggcgcat caccatgcgc aagactgctg       180
gcaagcccaa gccagcggcg tccggcagcc cctggtacgg ggccgaccgc gtcctgtacc       240
tgggcccgct gtccggccag ccccaagct acctgaccgg cgagttcccc ggcgactacg       300
gctgggacac cgcggggctg tccgccgacc cggagacttt cgccaagaac cgcgagctgg       360
aggtgatcca ctgccgctgg gccatgctgg gcgcgctcgg gtgcgtgttc ccggagctgc       420
tcgcccgcaa cggcgtcaag ttcggcgagg ccgtgtggtt caaggccggg tcccagatct       480
tcagcgaggg cgggcttgac tacctcggca cccgagcct gatccacgcg cagagcatcc       540
tggccatctg ggcgtgccag gtggtgctca tgggcgccgt cgaggggtac cgcatcgccg       600
gtggcccgct cggggaggtg gtcgaccgc tgtaccccgg cggcagcttc gacccgctcg       660
ggctcgccga cgacccggag gcgttcgcgg agctcaaggt caaggagatc aagaacggcc       720
gcctcgccat gttctccatg ttcggcttct tcgtgcaggc catcgtcacc ggcaagggtc       780
ccgttgagaa cctcgccgac cacctcgctg accctgtcaa caacaacgcc tgggcctacg       840
ctaccaactt cgtccccggc aagtgagcga gggcatatac atacttgtat gcgtgtaccg       900
tagacatacg tattcgtata tgtactgcag gagatgtacc agtatttgtg aagaagggag       960
catgggctca gagattgtac cagtagtgta cgtatttgca tgcatgcttt ggaaaaaaaa      1020
aaaaaaaaaa aaaaaaaaaa aaaaaaaaaa aaaaaaaaaa cctcgaattt gccaccttct      1080
tgctgtttta aaatatttt atcacttata tgctgcatta ggtggtagga gttgaatggt      1140
taaaccttg ctgcataact tccttgaatt attgagtatc aaggatgata                 1190
```

<210> SEQ ID NO 26
<211> LENGTH: 264
<212> TYPE: PRT
<213> ORGANISM: Zea mays

<400> SEQUENCE: 26

```
Met Ala Ala Ala Thr Met Ala Leu Thr Ser Arg Ala Leu Val Gly Lys
1               5                   10                  15

Pro Ala Thr Ser Thr Arg Asp Val Phe Gly Glu Gly Arg Ile Thr Met
                20                  25                  30

Arg Lys Thr Ala Gly Lys Pro Lys Pro Ala Ala Ser Gly Ser Pro Trp
            35                  40                  45

Tyr Gly Ala Asp Arg Val Leu Tyr Leu Gly Pro Leu Ser Gly Gln Pro
        50                  55                  60

Pro Ser Tyr Leu Thr Gly Glu Phe Pro Gly Asp Tyr Gly Trp Asp Thr
65                  70                  75                  80

Ala Gly Leu Ser Ala Asp Pro Glu Thr Phe Ala Lys Asn Arg Glu Leu
                85                  90                  95
```

```
Glu Val Ile His Cys Arg Trp Ala Met Leu Gly Ala Leu Gly Cys Val
                100                 105                 110
Phe Pro Glu Leu Leu Ala Arg Asn Gly Val Lys Phe Gly Glu Ala Val
            115                 120                 125
Trp Phe Lys Ala Gly Ser Gln Ile Phe Ser Glu Gly Gly Leu Asp Tyr
    130                 135                 140
Leu Gly Asn Pro Ser Leu Ile His Ala Gln Ser Ile Leu Ala Ile Trp
145                 150                 155                 160
Ala Cys Gln Val Val Leu Met Gly Ala Val Glu Gly Tyr Arg Ile Ala
                165                 170                 175
Gly Gly Pro Leu Gly Glu Val Val Asp Pro Leu Tyr Pro Gly Gly Ser
            180                 185                 190
Phe Asp Pro Leu Gly Leu Ala Asp Asp Pro Glu Ala Phe Ala Glu Leu
        195                 200                 205
Lys Val Lys Glu Ile Lys Asn Gly Arg Leu Ala Met Phe Ser Met Phe
    210                 215                 220
Gly Phe Phe Val Gln Ala Ile Val Thr Gly Lys Gly Pro Val Glu Asn
225                 230                 235                 240
Leu Ala Asp His Leu Ala Asp Pro Val Asn Asn Ala Trp Ala Tyr
                245                 250                 255
Ala Thr Asn Phe Val Pro Gly Lys
            260

<210> SEQ ID NO 27
<211> LENGTH: 2351
<212> TYPE: DNA
<213> ORGANISM: Zea mays

<400> SEQUENCE: 27
gaggaaggga tggccgggag cagcgtccgc ggcggcagca actgcccacc gctgttcgtg      60
acggagaaac caacgcggat ggcgaggtac gcttaccggc tgttcgcgag cacggtcctc     120
gcggggttc ttctggtatg ctgtacaga gcaacgcacg tgccgccgat gagcagcggc       180
gcccggtggt gggcgtggct tgggctctcc gcggcggagc tctggttcgg cttctactgg     240
gtgctgacgc tgtccgtgcg gtggagcccc gtcttccgcc gcgccttccc ggaccagctc     300
ttgcgaaggt acaaggaaga gcagcttcct ggggtggaca tatttgtgtg tacagcagac     360
cccactgttg agccgccaat gcttgtcatc tccactgtcc tatctgttat ggcttatgac     420
tacccgaagg agaagttgaa catatatttg tctgatgatg ctggttccat cataacattg     480
tatgctctat atgaagcatc agagtttgca aagcactggc ttccattttg caataagtac     540
caagtggagc ccaggtcacc agctgcctac tttggtacag aagctagccc tccagatgca     600
tgtgaccgta agagtggtt ttctttgaag gagatgcaca agatttggc agctcgagtg       660
aattcagttg ttaattcagg gaagatccct gaagtttcaa atgcaagct tatgggcttc      720
tccaggtgga gcgagaatgc aagttttaga gatcacccctt caatagttca gattttaatt   780
gatggaaaca aaggaaagc aactgatatc gatggaaaag tgttgcccac actggtttat     840
atggctcgtg agaagagacc tcaagaacat catcacttca agctggatc actgaatgct    900
ttgataaggg tatcatcggt gataagcaac agcccagtca ttatgaatgt ggactgtgat    960
atgtactcca caattcagg gtctatcaga gatgcattgt gcttcttcca agacgaacag    1020
ctaggtcaag atattgcttt tgttcagtat cctcagaact tcgaaaatgt ggtgcaaaat    1080
gacatctatg gcaatcccat caacaccgtc aatgagttgg accatccttg cttggatgga   1140
```

-continued

```
tggggtggaa tgtgttacta tggcacagga tgcttccatc ggagagaggc tctatgtggg    1200
cgaatataca gtccagacta caaggaagat tggactaggt ggcgaggaa aactgaagat     1260
gtcattgact tggaaggaat ggctgagtca cttgtgactt gcacatatga gcacaacacc    1320
ctttggggag tcgagaaggg agttatatat ggttgcccac tggaggatgt cattacagga    1380
ttgcagatcc agtgccgtgg gtggagatca gtttaccaca acccgccaag aaagggtttt   1440
ttaggcatgg cccctacctc actaggacag attctggttc agcacaagag atggacagaa    1500
gggttcctcc agatctccct ctcaaagtac agcccgtttc tgctaggtca caggaagatc    1560
agcctgggcc ttcaaatggg ttactccgtc tgcgggttct gggctgctaa cagcttcccc    1620
acccttact atgtcactat cccttcactt tgcttcctca atggcatctc attgttccct     1680
gagataacca gtccctggtt tgtaccgttt gcatacgttg ctgtggctgc atactcctgc    1740
agcttggtgg agtccctgca atgtggcgac actgctgttg agtggtggaa cgcgcaaagg    1800
atgtggcttt tcagaagaat cacctcatac ctcttggcag ccatcgacac aatccgcaga    1860
atgcttggcg tcaccgagtc ggggttcacc ctgacgacga aggtgaccga tccgcaggcc    1920
ctagagaggg acaagaaggg gatgatggag tttgggtcct tctccgcgat gtttgcgatc    1980
attacaaccg ttgcactgct taacctggcg tgcatgatgc tcggggtggc aaaggttttg    2040
ttgcgtaaag gagcggtgat gagtctggga gctatgtttg tgcaggccgt tctatgtgcg    2100
ctgatagtag cgatcaattt cccagtgtat gaagcaatgt tcgcccgcaa ggacagtggc    2160
agattaccag cttctgtcgg tgtagtttcg ctctgcattg tattgccatt ctgtatactt    2220
ccaaccaact tgtagatgtg gagctggtga agatgatat atatatttga aacccgatgg    2280
tgaaagttat aagaactgta ctgatataat atatttccaa gaaaatataa aaatctaaaa    2340
aaaaaaaaaa a                                                        2351
```

<210> SEQ ID NO 28
<211> LENGTH: 741
<212> TYPE: PRT
<213> ORGANISM: Zea mays

<400> SEQUENCE: 28

```
Met Ala Gly Ser Ser Val Arg Gly Gly Ser Asn Cys Pro Pro Leu Phe
1               5                   10                  15

Val Thr Glu Lys Pro Thr Arg Met Ala Arg Tyr Ala Tyr Arg Leu Phe
            20                  25                  30

Ala Ser Thr Val Leu Ala Gly Val Leu Val Trp Leu Tyr Arg Ala
        35                  40                  45

Thr His Val Pro Pro Met Ser Ser Gly Ala Arg Trp Trp Ala Trp Leu
    50                  55                  60

Gly Leu Ser Ala Ala Glu Leu Trp Phe Gly Phe Tyr Trp Val Leu Thr
65                  70                  75                  80

Leu Ser Val Arg Trp Ser Pro Val Phe Arg Ala Phe Pro Asp Gln
                85                  90                  95

Leu Leu Arg Arg Tyr Lys Glu Glu Gln Leu Pro Gly Val Asp Ile Phe
            100                 105                 110

Val Cys Thr Ala Asp Pro Thr Val Glu Pro Pro Met Leu Val Ile Ser
        115                 120                 125

Thr Val Leu Ser Val Met Ala Tyr Asp Tyr Pro Lys Glu Lys Leu Asn
    130                 135                 140

Ile Tyr Leu Ser Asp Asp Ala Gly Ser Ile Ile Thr Leu Tyr Ala Leu
145                 150                 155                 160
```

-continued

```
Tyr Glu Ala Ser Glu Phe Ala Lys His Trp Leu Pro Phe Cys Asn Lys
                165                 170                 175

Tyr Gln Val Glu Pro Arg Ser Pro Ala Ala Tyr Phe Gly Thr Glu Ala
            180                 185                 190

Ser Pro Pro Asp Ala Cys Asp Arg Lys Glu Trp Phe Ser Leu Lys Glu
        195                 200                 205

Met His Lys Asp Leu Ala Ala Arg Val Asn Ser Val Val Asn Ser Gly
    210                 215                 220

Lys Ile Pro Glu Val Ser Lys Cys Lys Leu Met Gly Phe Ser Arg Trp
225                 230                 235                 240

Ser Glu Asn Ala Ser Phe Arg Asp His Pro Ser Ile Val Gln Ile Leu
                245                 250                 255

Ile Asp Gly Asn Lys Arg Lys Ala Thr Asp Ile Asp Gly Lys Val Leu
            260                 265                 270

Pro Thr Leu Val Tyr Met Ala Arg Glu Lys Arg Pro Gln Glu His His
        275                 280                 285

His Phe Lys Ala Gly Ser Leu Asn Ala Leu Ile Arg Val Ser Ser Val
    290                 295                 300

Ile Ser Asn Ser Pro Val Ile Met Asn Val Asp Cys Asp Met Tyr Ser
305                 310                 315                 320

Asn Asn Ser Gly Ser Ile Arg Asp Ala Leu Cys Phe Phe Gln Asp Glu
                325                 330                 335

Gln Leu Gly Gln Asp Ile Ala Phe Val Gln Tyr Pro Gln Asn Phe Glu
            340                 345                 350

Asn Val Val Gln Asn Asp Ile Tyr Gly Asn Pro Ile Asn Thr Val Asn
        355                 360                 365

Glu Leu Asp His Pro Cys Leu Asp Gly Trp Gly Gly Met Cys Tyr Tyr
    370                 375                 380

Gly Thr Gly Cys Phe His Arg Arg Glu Ala Leu Cys Gly Arg Ile Tyr
385                 390                 395                 400

Ser Pro Asp Tyr Lys Glu Asp Trp Thr Arg Val Ala Arg Lys Thr Glu
                405                 410                 415

Asp Val Ile Asp Leu Glu Gly Met Ala Glu Ser Leu Val Thr Cys Thr
            420                 425                 430

Tyr Glu His Asn Thr Leu Trp Gly Val Glu Lys Gly Val Ile Tyr Gly
        435                 440                 445

Cys Pro Leu Glu Asp Val Ile Thr Gly Leu Gln Ile Gln Cys Arg Gly
    450                 455                 460

Trp Arg Ser Val Tyr His Asn Pro Pro Arg Lys Gly Phe Leu Gly Met
465                 470                 475                 480

Ala Pro Thr Ser Leu Gly Gln Ile Leu Val Gln His Lys Arg Trp Thr
                485                 490                 495

Glu Gly Phe Leu Gln Ile Ser Leu Ser Lys Tyr Ser Pro Phe Leu Leu
            500                 505                 510

Gly His Arg Lys Ile Ser Leu Gly Leu Gln Met Gly Tyr Ser Val Cys
        515                 520                 525

Gly Phe Trp Ala Ala Asn Ser Phe Pro Thr Leu Tyr Tyr Val Thr Ile
    530                 535                 540

Pro Ser Leu Cys Phe Leu Asn Gly Ile Ser Leu Phe Pro Glu Ile Thr
545                 550                 555                 560

Ser Pro Trp Phe Val Pro Phe Ala Tyr Val Ala Val Ala Ala Tyr Ser
                565                 570                 575
```

```
Cys Ser Leu Val Glu Ser Leu Gln Cys Gly Asp Thr Ala Val Glu Trp
            580                 585                 590

Trp Asn Ala Gln Arg Met Trp Leu Phe Arg Arg Ile Thr Ser Tyr Leu
        595                 600                 605

Leu Ala Ala Ile Asp Thr Ile Arg Arg Met Leu Gly Val Thr Glu Ser
    610                 615                 620

Gly Phe Thr Leu Thr Thr Lys Val Thr Asp Pro Gln Ala Leu Glu Arg
625                 630                 635                 640

Tyr Lys Lys Gly Met Met Glu Phe Gly Ser Phe Ser Ala Met Phe Ala
                645                 650                 655

Ile Ile Thr Thr Val Ala Leu Leu Asn Leu Ala Cys Met Met Leu Gly
            660                 665                 670

Val Ala Lys Val Leu Leu Arg Lys Gly Ala Val Met Ser Leu Gly Ala
        675                 680                 685

Met Phe Val Gln Ala Val Leu Cys Ala Leu Ile Val Ala Ile Asn Phe
    690                 695                 700

Pro Val Tyr Glu Ala Met Phe Ala Arg Lys Asp Ser Gly Arg Leu Pro
705                 710                 715                 720

Ala Ser Val Gly Val Val Ser Leu Cys Ile Val Leu Pro Phe Cys Ile
                725                 730                 735

Leu Pro Thr Asn Leu
            740

<210> SEQ ID NO 29
<211> LENGTH: 2318
<212> TYPE: DNA
<213> ORGANISM: Zea mays

<400> SEQUENCE: 29
tctagacgca cacagacaga aagagtcggt acaaatcgtc gagggaggcc gggcgcgcgt      60
aggaacagaa agacacgcag ccagattgac agagctgagt gtgagtacgt actacgtaga     120
tacctacagc tatactgtac tgtacagagt gggaggaaaa gggagggaga gagagggacg     180
tgtacacaca cgcgcgtaca aaaatacaga ggaagcttag cttgcctcca accccgaccg     240
acactcgggc tcgtgaaccc cgtcccgtaa tttctctata tatcccgtcc ctccccccac     300
gtacttcact cggcctccat ctccccacgc acccggcgc ccgcgccgcg ccacttctc      360
tcccccctcc tcctcctcct ctctctctct ctctctctct gccacacagc acaccagaag     420
ggcagcaggg gaggtagaga gaggtagctt cgcattctcg gtttccctcc gcgcgtgtcc     480
tcccagcctc gacagagaga agggccacca tcgtccctgc ctgattgcgc gccaggcagg     540
caggcattat ggcgccgggc ggccggcgca gcaacggcga gacgccgaca ggacagcagc     600
agcagcagca gcaggctgac ggcaggcgcg ggtgcgcatg cggcgggttc ccgtgtgcg      660
cgtgcgccgg cgcggcggcg gtggcgtccg ccgcctcctc cgccgacatg gaccgcgtgg     720
cggtggccgc caccgagggc cagatcggcg ccgtcaacga cgagagctgg gtggcggtcg     780
acctcagcga cgacggcctc tcctccgccg ccgacccggg ggccgtcgcg ctcgaggaac     840
gccccgtctt ccgcaccgag aagatcaagg gtgtcctcct ccaccccatc agggtgctca     900
tcttcgtgcg cctgatcgcg ttcacgctgt tcgtgatctg gcgcatctcg caccgcaacc     960
cggacgcgct gtggctgtgg gtgacgtcga tcgcgggcga gttctggttc ggcttctcgt    1020
ggctgctgga ccagctgccg aagctgaacc cgatcaaccg cgtgccggac ctggggcgc     1080
tgcggcagcg gttcgaccgc gccgacggga cgtcgcggct gccggggctg acatcttcg     1140
```

```
tgaccacggc ggacccgttc aaggagccga tcctgagcac ggccaactcc atcctctcca   1200
tcctggccgc cgactacccc gtggagcgca acacgtgcta cctctccgac gactcgggca   1260
tgctgctcac gtacgaggcc atggcggagg ccgccaagtt cgccaccgtc tgggtgccct   1320
tctgccgcaa gcacggcatc gagccgcgcg ccccgagag ctacttcgag ctcaagtccc    1380
accctacat gggccgctcc caggaggact tcgtcaacga ccgccgccgc gtgcgcaggg    1440
actacgacga gttcaaggcg cgcatcaacg ggctggagaa cgacatcagg cagcgctccg   1500
acgcctacaa cgccgccagg gggctcaagg acggcgagcc cagggctacg tggatggccg   1560
acggcacaca gtgggagggc acctgggttg agccgtccga gaaccaccgc aagggcgacc   1620
atgccggcat cgtcctggtg cttctgaacc acccgagcca cagccgtcag ctcgggccgc   1680
cggcgagcgc ggacaacccg ctggacttga gcatggtgga cgtgcggctc cccatgctgg   1740
tgtacgtctc ccgcgagaag cggcccgggc acaaccacca gaagaaggcc ggcgccatga   1800
acgcgctgac ccgtgctcc gccgtgctct ccaactcgcc cttcatcctg aacctggact    1860
gcgaccacta catcaacaac tcgcaggcgc tgcgcgcggg catctgcttc atgctcgggc   1920
gggacagcga cacggtggcg ttcgtccagt tcccgcagcg cttcgagggc gtggaccccca  1980
cggacctgta cgccaaccac aaccgcatct tcttcgacgg cacgctccgg gcgctggacg   2040
gcatgcaggg ccccatctac gtcggcacgg gctgcctgtt ccgccgcatc acgctctacg   2100
gcttcgaccc gccgcggatc aacgtgggcg ggccgtgctt cccgtcgctg ggcggcatgt   2160
tcgccaagac caagtacgag aagcctgggc tggagctcac caccaaggcc gccgtggcca   2220
agggcaagca cggcttcctg cccatgccca agaagtcgta cggcaagtcg gacgcgttcg   2280
cggacaccat cccgatggcg tcgcacccgt cgccgttc                           2318
```

<210> SEQ ID NO 30
<211> LENGTH: 590
<212> TYPE: PRT
<213> ORGANISM: Zea mays

<400> SEQUENCE: 30

```
Met Ala Pro Gly Gly Arg Arg Ser Asn Gly Glu Thr Pro Thr Gly Gln
 1               5                  10                  15

Gln Gln Gln Gln Gln Ala Asp Gly Arg Arg Gly Cys Ala Cys Gly
            20                  25                  30

Gly Phe Pro Val Cys Ala Cys Ala Gly Ala Ala Val Ala Ser Ala
        35                  40                  45

Ala Ser Ser Ala Asp Met Asp Arg Val Ala Val Ala Thr Glu Gly
    50                  55                  60

Gln Ile Gly Ala Val Asn Asp Glu Ser Trp Val Ala Val Asp Leu Ser
65                  70                  75                  80

Asp Asp Gly Leu Ser Ser Ala Ala Asp Pro Gly Ala Val Ala Leu Glu
                85                  90                  95

Glu Arg Pro Val Phe Arg Thr Glu Lys Ile Lys Gly Val Leu Leu His
            100                 105                 110

Pro Tyr Arg Val Leu Ile Phe Val Arg Leu Ile Ala Phe Thr Leu Phe
        115                 120                 125

Val Ile Trp Arg Ile Ser His Arg Asn Pro Asp Ala Leu Trp Leu Trp
    130                 135                 140

Val Thr Ser Ile Ala Gly Glu Phe Trp Phe Gly Phe Ser Trp Leu Leu
145                 150                 155                 160
```

```
Asp Gln Leu Pro Lys Leu Asn Pro Ile Asn Arg Val Pro Asp Leu Gly
            165                 170                 175
Ala Leu Arg Gln Arg Phe Asp Arg Ala Asp Gly Thr Ser Arg Leu Pro
        180                 185                 190
Gly Leu Asp Ile Phe Val Thr Thr Ala Asp Pro Phe Lys Glu Pro Ile
    195                 200                 205
Leu Ser Thr Ala Asn Ser Ile Leu Ser Ile Leu Ala Ala Asp Tyr Pro
210                 215                 220
Val Glu Arg Asn Thr Cys Tyr Leu Ser Asp Asp Ser Gly Met Leu Leu
225                 230                 235                 240
Thr Tyr Glu Ala Met Ala Glu Ala Ala Lys Phe Ala Thr Val Trp Val
                245                 250                 255
Pro Phe Cys Arg Lys His Gly Ile Glu Pro Arg Gly Pro Glu Ser Tyr
            260                 265                 270
Phe Glu Leu Lys Ser His Pro Tyr Met Gly Arg Ser Gln Glu Asp Phe
        275                 280                 285
Val Asn Asp Arg Arg Val Arg Arg Asp Tyr Asp Glu Phe Lys Ala
    290                 295                 300
Arg Ile Asn Gly Leu Glu Asn Asp Ile Arg Gln Arg Ser Asp Ala Tyr
305                 310                 315                 320
Asn Ala Ala Arg Gly Leu Lys Asp Gly Glu Pro Arg Ala Thr Trp Met
                325                 330                 335
Ala Asp Gly Thr Gln Trp Glu Gly Thr Trp Val Glu Pro Ser Glu Asn
            340                 345                 350
His Arg Lys Gly Asp His Ala Gly Ile Val Leu Val Leu Asn His
        355                 360                 365
Pro Ser His Ser Arg Gln Leu Gly Pro Pro Ala Ser Ala Asp Asn Pro
    370                 375                 380
Leu Asp Leu Ser Met Val Asp Val Arg Leu Pro Met Leu Val Tyr Val
385                 390                 395                 400
Ser Arg Glu Lys Arg Pro Gly His Asn His Gln Lys Lys Ala Gly Ala
                405                 410                 415
Met Asn Ala Leu Thr Arg Cys Ser Ala Val Leu Ser Asn Ser Pro Phe
            420                 425                 430
Ile Leu Asn Leu Asp Cys Asp His Tyr Ile Asn Asn Ser Gln Ala Leu
        435                 440                 445
Arg Ala Gly Ile Cys Phe Met Leu Gly Arg Asp Ser Asp Thr Val Ala
    450                 455                 460
Phe Val Gln Phe Pro Gln Arg Phe Glu Gly Val Asp Pro Thr Asp Leu
465                 470                 475                 480
Tyr Ala Asn His Asn Arg Ile Phe Phe Asp Gly Thr Leu Arg Ala Leu
                485                 490                 495
Asp Gly Met Gln Gly Pro Ile Tyr Val Gly Thr Gly Cys Leu Phe Arg
            500                 505                 510
Arg Ile Thr Leu Tyr Gly Phe Asp Pro Pro Arg Ile Asn Val Gly Gly
        515                 520                 525
Pro Cys Phe Pro Ser Leu Gly Gly Met Phe Ala Lys Thr Lys Tyr Glu
    530                 535                 540
Lys Pro Gly Leu Glu Leu Thr Thr Lys Ala Ala Val Ala Lys Gly Lys
545                 550                 555                 560
```

```
-continued

His Gly Phe Leu Pro Met Pro Lys Lys Ser Tyr Gly Lys Ser Asp Ala
            565                 570                 575

Phe Ala Asp Thr Ile Pro Met Ala Ser His Pro Ser Pro Phe
            580                 585             590
```

MANIPULATION OF PLANT POLYSACCHARIDE SYNTHASES

CROSS-REFERENCE TO RELATED APPLICATIONS

This application is a continuation of U.S. application Ser. No. 10/260,046 filed Sep. 27, 2002, now issued as U.S. Pat No. 7,098,380, which claims the benefit of U.S. application Ser. No. 60/325,614 filed Sep. 27, 2001, which is herein incorporated by reference.

FIELD OF THE INVENTION

The present invention relates to polysaccharide production in plants through alteration of the polysaccharide synthesis pathways.

BACKGROUND OF THE INVENTION

Cereals constitute a major portion of human nutrition because of the polysaccharides the plants produce. Annually, over one billion tons of cereal grains are harvested, and half the calories consumed by humans are from rice and wheat alone. In addition, grazing animals consume vast amounts of grasses. Although cellulose is the primary polysaccharide of plants, plant cell walls also contain hemicelluloses and pectins (Carpita (1996) *Annu. Rev. Plant Physiol. Plant Mol. Biol.* 47:445-476).

Plant growth is determined by concerted synthesis of cell wall polymers, such as hemicelluloses and pectins. Thus, increased synthesis of one cell wall polymer is expected to cause an increase in the synthesis of the other polymers as well. Increased production of a plant polysaccharide generally accelerates plant growth. Conversely, decreased production of a plant polysaccharide generally inhibits the synthesis of other cell wall polymers and slows plant growth.

Mature plant cells generally contain about 30-40% hemicellulose. In monocot species, arabinoxylan (also referred to as glucurono-arabinoxylans or pentosan) is the main component of hemicellulose in the cell wall. In contrast, dicot cell walls contain xyloglucan as the primary hemicellulosic polymer (Carpita (1996) *Annu. Rev. Plant Physiol. Plant Mol. Biol.* 47:445-476).

Arabinoxylans are anti-nutritional components of animal feed, yet these polymers constitute 45-65% of the plant cell wall. Arabinoxylans absorb large amounts of water thus increasing the viscosity of the chyme and sequestering other digestible nutrients away from the digestive enzymes (WO 99/67404). In addition, the increased viscosity of the chyme results in sticky feces that contribute to animal hygiene and enteric disturbance problems for the livestock producer (Selinger et al. (1996) *Anaerobe* 2:263-284). Therefore, in certain circumstances, it would be desirable to lower the concentration of arabinoxylans in plants.

However, dietary fiber, particularly arabinoxylan, reduces cholesterol and low density lipoprotein levels in humans (WO 99/67,404). In breadmaking, bread quality depends heavily on the consistency of the dough. Dough that lacks viscosity alters the crumb structure of the bread and decreases the volume of bread produced. Arabinoxylan provides the viscous properties of dough (Girhammar et al. (1995) *Food Hydrocolloids* 9:133-140). Additionally, industries use isolated arabinoxylan preparations as thickeners, emulsifiers, or stabilizers in food, cosmetics, and pharmaceuticals. Therefore, in certain circumstances, it would be desirable to increase the concentration of arabinoxylans in plant.

The modulation of hemicellulose content can also be utilized to control plant growth. For example, plant growth is determined by concerted synthesis of cell wall polymers. It is expected that increased synthesis of one of the cell wall polymers, such as hemicellulose, will cause an increase in the synthesis of the rest of the polymers as well. It is expected that increased production of arabinoxylan or xyloglucan in vegetative tissue will accelerate plant growth. In contrast, it is expected that decreased production of arabinoxylan will slow plant growth. Additionally, tissue-specific control of hemicellulose productivity is used to modify plant organ growth and development. Early flowering, larger fruit size, or stronger stalk or stem quality is achieved by operably linking a tissue specific promoter to a gene which when expressed increases hemicellulose biosynthesis (U.S. Pat. No. 6,194, 638). In view of the foregoing, it would be desirable to modulate the arabinoxylan and xyloglucan concentration in crop plants.

Clearly, modulating the concentrations of polysaccharides in various crops is a desirable goal. However, a direct approach using the enzymes that synthesize polysaccharides has been obscured for some time due to difficulties in isolating and cloning any of the plant polysaccharide synthase genes. Polysaccharide synthase enzymes for the common polysaccharides are estimated to number in the hundreds. Recently, several cellulose-synthase genes have been identified. The cellulose synthase genes share regions of homology that allow the identification of novel genes that participate in polysaccharide synthesis (Cutler et al. (1997) *Current Biology* 7: R108-R111).

Compositions and methodologies useful in the modulation of polysaccharide levels in plants are needed.

SUMMARY OF THE INVENTION

Compositions and methods for modulating plant polysaccharide synthesis are provided. In particular, the present invention provides nucleotide sequences encoding polysaccharide synthase polypeptides. More specifically, the present invention provides the nucleotide sequences set forth in SEQ ID NOS: 1, 3, 5, 7, 9, 11, 13, 15, 17, 19, 21, 23, 25, 27, 29 or variants thereof. Also provided are amino acid sequences (SEQ ID NOS: 2, 4, 6, 8, 10, 12, 14, 16, 18, 20, 22, 24, 26, 28, 30) encoded by the nucleotide sequences of the invention, and biologically active variants thereof.

Further compositions of the invention include expression cassettes and vectors for expression of these novel sequences in plants. Transformed plant cells, plants, plant tissues, and seed are also provided.

The invention further provides a method for modulation of polysaccharides, particularly hemicelluloses and pectins in plants. The method comprises stably incorporating into the genome of a plant a nucleotide sequence encoding a polypeptide of the invention operably linked to a promoter that drives expression of the sequence in the plant. Modification of plant polysaccharide levels alters the digestability and nutritive value of the plant and improves the sanitation of livestock and poultry that have consumed the plant. Additionally, modification of plant polysaccharide levels alters plant growth and allows extraction of gums.

DETAILED DESCRIPTION OF THE INVENTION

The present invention provides compositions and methods for the modulation of polysaccharides in a plant. Compositions are nucleic acid molecules comprising novel nucleotide sequences encoding polypeptides that are involved in polysaccharide synthesis, hereinafter referred to as "polysaccharide synthases." Specifically, the present invention provides for isolated nucleic acid molecules comprising nucleotide sequences encoding the amino acid sequences shown in SEQ ID NOS: 2, 4, 6, 8, 10, 12, 14, 16, 18, 20, 22, 24, 26, 28, or 30 or the nucleotide sequences encoding the cDNA insert of the plasmids deposited in a bacterial host as Patent Deposit Nos. PTA-3610, PTA-3612, PTA-3611, or PTA-3613. Further provided are polypeptides having an amino acid sequence encoded by the nucleic acid molecules described herein, for example those set forth in SEQ ID NOS: 1, 3, 5, 7, 9, 11, 13, 15, 17, 19, 21, 23, 25, 27,or 29, and fragments and variants thereof. These nucleotide sequences were identified in *Zea mays*.

Plasmids containing several of the nucleotide sequences of the invention were deposited with the Patent Depository of the American Type Culture Collection (ATCC), Manassas, Va., on Aug. 7, 2001 and assigned Patent Deposit Nos. PTA-3610, PTA-3612, PTA-3611, or PTA-3613. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

By "polysaccharide synthase" is intended the polypeptides of the invention that are enzymes involved in the synthesis of polysaccharides. By "polysaccharide synthesis" or "synthesis of polysaccharide(s)" is intended any modification to a polymer of monosaccharide residues including, but not limited to, xylose, glucose, arabinose, mannose, and galactose. Such modifications include ligation or formation of any of the various bonds, oxidation, reduction, the addition or deletion of a chemical moiety, particularly glucuronic acid, arabinose, acetyl, galactose, xylose, fucose, mannose, and rhamnose side chains, or any other change that affects the structure or activity of the molecule, including rerouting a polysaccharide from one biosynthetic pathway to another. While the present invention is not bound by any particular mechanism of polysaccharide synthesis, the sequences of the invention may synthesize polysaccharides by catalyzing glycosidic linkages extending the polysaccharide polymer, attaching side chain residues, or modifying the side chains of the polysaccharide. Hence polypeptides having polysaccharide synthase activity are characterized by the ability to accelerate the chemical modification of a polysaccharide molecule. Rerouting a polysaccharide from one biosynthetic pathway to another results in an increase or decrease in the level of another polysaccharide, and hence alters polysaccharide composition of a plant cell, tissue, or organ.

The polysaccharide synthases of the invention are characterized by their sequence similarity to previously identified enzymes that are known to be involved in polysaccharide synthesis. Such enzymes include, for example, celA1 (Pear et al. (1996) *Proc. Natl. Acad. Sci.* 93:12637-12642; Richmond et al. (2000) *Plant Physiol.* 124: 495-498), which is a cellulose synthase-like (Csl) polypeptide. The Csl polypeptides share amino-acid-sequence homology to known cellulose synthases. The Csl polypeptides contain a QxxRW motif, which may form the substrate binding and catalytic sites of these enzymes (Richmond et al, (2000) *Plant Physiology* 124: 495-498), as well as 3-6 transmembrane domains at the carboxy-terminus and 1-2 transmembrane domains at the amino-terminus. Transmembrane domains anchor polypeptides to membranes, including, for example, the Golgi apparatus membrane. The polypeptides responsible for synthesis of polysaccharides other than cellulose and callose, such as hemicelluloses and pectins, are membrane-associated (WO 99/67404). In fact, polypeptides encoded by several Csl genes have been localized to the Golgi apparatus and endoplasmic reticulum where synthesis of polysaccharides occurs (Favery et al. (2001) *Genes Dev.* 15:79-89; Ray et al. (1976) *Ber. Deutsch Bot. Ges. Bd.* 89:1.21-146 [cited in WO 99/67404]).

The novel polysaccharide synthases of the invention have several features in common with Csl polypeptides known in the art. These novel polypeptides contain the QxxRW motif and at least 4 transmembrane domains. The nucleotide sequences of the invention (SEQ ID NOS: 1, 3, 5, 7, 9, 11, 13, 15, 17, 19, 21, 23, 25, 27, 29) encode polypeptides that contain 6 transmembrane domains. The Golgi localization of the polypeptides encoded by the polysaccharide synthase nucleotide sequences of the invention suggests these polysaccharide synthases are more likely to synthesize polysaccharides such as hemicelluloses or pectins rather than cellulose or callose (Richmond et al. (2000) *Plant Physiology* 124: 495-498). This CS1F class of genes is responsible for making the xylan backbone of arabinoxylan, and in so doing provides for changes in maize stalk and other tissues. Hence, the sequences of the invention may find use in the modulation of polysaccharide levels, thereby altering overall polysaccharide composition of a plant cell, tissue, or organ.

Polysaccharides predominate in the cell wall of plants and are grouped in several classes, including hemicellulose and pectin. The hemicellulose class of polysaccharides cannot be extracted from the plant cell wall with water or chelating agents, but can be extracted with aqueous alkali. The hemicelluloses include polysaccharides selected from the group comprised of xylans, glucuronoxylans, arabinoxylans, arabinogalactans II, glucomannans, xyloglucans, mixed-link glucans, and galactomannans. Xylans contain a backbone of (1,4)-linked xylose residues with side chains present in varying amounts. In glucuronoxylans, glucuronic acid side chains predominate, although the compound may contain arabinose and acetyl side chains also. In arabinoxylans, arabinose side chains predominate. Glucomannans contain glucose and xylose linked by 1,4-glycosidic bonds, and galactose side chains are possible. Xyloglucans contain a backbone of (1,4)-linked glucose residues with xylose side chains, although galactose, fucose, and arabinose side chains are possible.

The pectin class of polysaccharides can be extracted from the plant cell wall with hot aqueous solutions of chelating agents or with hot dilute acid. Pectin includes polysaccharides rich in galacturonic acid, rhamnose, arabinose, and galactose, such as polygalacturonans, rhamnogalacturonans, and some arabinans, galactans, and arabinogalactans. Polygalacturonans consist primarily of galacturonic acid. Rhamnogalacturonans consist predominantly of galacturonic acid and rhamnose, although some forms may have up to four additional types of sugar. Galactans are polymers of galactose.

The quantity and complexity of plant polysaccharides has slowed development in the understanding of their biosynthetic pathways. The quantity and permutations of linkages, side chain patterns, and various backbones in polysaccharides suggests that the number of polysaccharide synthases is substantial. Numerous polysaccharide synthesis enzymatic activities have been identified including, but not limited to, xyloglucan alpha,1-2 fucosyltransferase; galactinol synthase; KOJAK; sucrose:sucrose 1-fructosyltransferase; fructan:fructan 1-fructosyltransferase; and Suc:fructan-6-fructosyltransferase. See Wulff et al. (2000) *Plant Physiol.* 122:867-877; Sprenger et al. (2000) *Plant J.* 21:249-258; Favery et al. (2001) *Genes Dev.* 15:79-89; Reid (2000) *Curr. Opin. Plant Biol.* 3:512-516; Hellwege et al. (2000) *Proc. Natl. Acad. Sci.*

15:8699-8704; Muller et al. (2000) *Plant Physiol.* 123:265-274; Geshi et a. (2000) *Planta* 210:622-629, and U.S. Pat. No. 6,194,638, each of which is herein incorporated by reference.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, preferably culture medium represents less than about 30%, 20%, 10%, 5%, or 1% (by dry weight) of chemical precursors or non-protein-of-interest chemicals.

Fragments and variants of the disclosed nucleotide sequences and polysaccharide synthase polypeptides encoded thereby are also encompassed by the present invention. By "fragment" is intended a portion of the nucleotide sequence or a portion of the amino acid sequence and hence polypeptide encoded thereby. Fragments of a nucleotide sequence may encode protein fragments that retain the activity of polysaccharide synthase polypeptides and hence function in polysaccharide synthesis. Alternatively, fragments of a nucleotide sequence that are useful as hybridization probes generally do not encode protein fragments retaining the activity of polysaccharide synthases. Furthermore, fragments used to decrease the activity of a polypeptide involved in polysaccharide synthesis using antisense or cosuppression technology also may not encode a polypeptide having the activity of polysaccharide synthases. However, expression of such fragments does result in a decrease in activity of a polypeptide involved in polysaccharide synthesis.

Generally, fragments of a nucleotide sequence will retain biological activity or encode a polypeptide that retains biological activity wherein "biological activity" is defined as any activity or function of the sequences of the invention, including, but not limited to: hybridization capability, the ability to prime synthesis, the ability to be specifically labeled, cellular activity, enzymatic activity, antigen activity, and binding activity. Thus, fragments of a nucleotide sequence of the invention may range from at least about 16 nucleotides, about 20 nucleotides, about 50 nucleotides, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, or up to 1919 nucleotides for SEQ ID NO: 1; at least about 16 nucleotides, about 20 nucleotides, about 50 nucleotides, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, or up to 1569 nucleotides for SEQ ID NO:3, the coding sequence set forth in SEQ ID NO:1; at least about 16 nucleotides, about 20 nucleotides, about 50 nucleotides, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, or up to 1673 nucleotides for SEQ ID NO:5; at least about 16 nucleotides, about 20 nucleotides, about 50 nucleotides, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, or up to 1611 nucleotides for SEQ ID NO:7, the coding sequence set forth in SEQ ID NO:5; at least about 16 nucleotides, about 20 nucleotides, about 50 nucleotides, 100, 150, 200, 250, 300, 350, 400, 450, 500, 550, 600, 650, 700, 750, 800, 850, 900, 950, 1000, 1050, 1100, 1150, 1200, or up to 1221 nucleotides for SEQ ID NO:9; at least about 16 nucleotides, about 20 nucleotides, about 50 nucleotides, 100, 150, 200, 250, 300, 350, 400, 450, 500, 550, 600, 650, 700, 750, 800, 850, 900, 950, 1000, 1050, or up to 1065 nucleotides for SEQ ID NO:11, the coding sequence set forth in SEQ ID NO:9; or at least about 16 nucleotides, about 20 nucleotides, about 50 nucleotides, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, or up to 1899 nucleotides for SEQ ID NO:13; at least about 16 nucleotides, about 20 nucleotides, about 50 nucleotides, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, or up to 1587 nucleotides for SEQ ID NO:15, the coding sequence set forth in SEQ ID NO:13, at least about 16 nucleotides, about 20 nucleotides, about 50 nucleotides, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, or up to 2551 nucleotides for SEQ ID NO: 17, at least about 16 nucleotides, about 20 nucleotides, about 50 nucleotides, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, or up to 1740 nucleotides for SEQ ID NO:19, at least about 16 nucleotides, about 20 nucleotides, about 50 nucleotides, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, or up to 1834 nucleotides for SEQ ID NO:21, at least about 16 nucleotides, about 20 nucleotides, about 50 nucleotides, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, or up to 2432 nucleotides for SEQ ID NO: 23, at least about 16 nucleotides, about 20 nucleotides, about 50 nucleotides, 100, 150, 200, 250, 300, 350, 400, 450, 500, 550, 600, 650, 700, 750, 800, 850, 900, 950, 1000, 1050, 1100, 1150, or up to 1190 nucleotides for SEQ ID NO: 25, at least about 16 nucleotides, about 20 nucleotides, about 50 nucleotides, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550,1600, 1650, 1700, 1750, 1800, 1850, 1900, 1950, 2000, 2050, 2100, 2150, 2200, 2250, 2300 or up to 2351 nucleotides for SEQ ID NO: 27, or at least about 16 nucleotides, about 20 nucleotides, about 50 nucleotides, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, or up to 2318 nucleotides for SEQ ID NO: 29. Alternatively, a nucleic acid molecule that is a fragment of a polysaccharide synthase nucleotide sequence of the present invention comprises a nucleotide sequence consisting of nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-1919 of SEQ ID NO: 1; nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1569 for SEQ ID NO:3; nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1673 of SEQ ID NO:5; nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1611 of SEQ ID NO:7; nucleotides 1-100, 100-200, 200-300, 300-400, 400-500, 500-600, 600-700, 700-800, 800-900, 900-1000, 1000-1100, 1100-1200, 1200-1221 of SEQ ID NO:9; nucleotides 1-100, 100-200, 200-300, 300-400, 400-500, 500-600, 600-700, 700-800, 800-900, 900-1000, 1000-1065 of SEQ ID NO:11; nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1899 of SEQ ID NO:13; nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1587 of SEQ ID NO:15, nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2100, 2100-2200, 2200-2300, 2300-2400, 2400-2500, 2500-2551 of SEQ ID NO:17, nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1740 of SEQ ID NO: 19, nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1834 of SEQ ID NO: 21, nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2100, 2100-2200, 2200-2300, 2300-2400, 2400-2432 of SEQ ID NO: 23, nucleotides 1-100, 100-200, 200-300, 300-400, 400-500, 500-600, 600-700, 700-800, 800-900, 900-1000, 1000-1100, 1100-1190 of SEQ ID NO: 25, nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2100, 2100-2200, 2200-2300, 2300-2351 of SEQ ID NO: 27, or nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2100, 2100-2200, 2200-2300, 2300-2318 of SEQ ID NO:29.

A fragment of a polysaccharide synthase nucleotide sequence that encodes a biologically active portion of a polysaccharide synthase polypeptide of the invention will encode at least 15, 25, 30, 50, 100, 150, 200, 250, 300, 350, 400, 450, 500, or up to 522 contiguous amino acids present in SEQ ID NO: 2 or SEQ ID NO: 4; at least 15, 25, 30, 50, 100, 150, 200, 250, 300, 350, 400, 450, 500, or up to 536 contiguous amino acids present in SEQ ID NO: 6 or SEQ ID NO: 8; at least 15, 25, 30, 50, 100, 150, 200, 250, 300, 350, or up to 354 contiguous amino acids present in SEQ ID NO:10 or SEQ ID NO:12; at least 15, 25, 30, 50, 100, 150, 200, 250, 300, 350, 400, 450, 500, or up to 528 contiguous amino acids present in SEQ ID NO:14 or SEQ ID NO:16, at least 15, 25, 30, 50, 100, 150, 200, 250, 300, 350, 400, 450, 500, 550, 600, 650, 700, or up to 720 contiguous amino acids present in SEQ ID NO: 18, at least 15, 25, 30, 50, 100, 150, 200, 250, 300, 350, 400, 450, 500, or up to 537 contiguous amino acids present in SEQ ID NO: 20, at least 15, 25, 30, 50, 100, 150, 200, 250, 300, 350, 400, 450, 500, 550 or up to 572 contiguous amino acids present in SEQ ID NO: 22, at least 15, 25, 30, 50, 100, 150, 200, 250, 300, 350, 400, 450, 500, 550, 600, 650, 700, or up to 727 contiguous amino acids present in SEQ ID NO: 24, at least 15, 25, 30, 50, 100, 150, 200, 250, or up to 264 contiguous amino acids present in SEQ ID NO: 26, at least 15, 25, 30, 50, 100, 150, 200, 250, 300, 350, 400, 450, 500, 550, 600, 650, 700, or up to 741 contiguous amino acids present in SEQ ID NO: 28, at least 15, 25, 30, 50, 100, 150, 200, 250, 300, 350, 400, 450, 500, 550 or up to 590 contiguous amino acids present in SEQ ID NO: 30. Fragments of a polysaccharide synthase nucleotide sequence that are useful as hybridization probes or PCR primers generally need not encode a polypeptide that retains polysaccharide synthase activity.

Thus, a fragment of a polysaccharide synthase nucleotide sequence may encode a biologically active portion of a polysaccharide synthase polypeptide, or it may be a fragment that can be used as a hybridization probe or PCR primer using methods disclosed below. A biologically active portion of a polysaccharide synthase polypeptide can be prepared by isolating a portion of one of the nucleotide sequences of the invention, expressing the encoded portion of the polysaccharide synthase polypeptide (e.g., by recombinant expression in vitro), and assessing the activity of the encoded portion of the polysaccharide synthase polypeptide.

Variants of the novel nucleotide sequences or polypacchaide synthase polypeptides encoded thereby are also encompassed by the present invention. By "variants" is intended substantially similar sequences. For nucleotide sequences, conservative variants include those sequences that, because of the degeneracy of the genetic code, encode the amino acid sequence of one of the polysaccharide synthase polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a polysaccharide synthase polypeptide of the invention. Generally, variants of a particular nucleotide sequence of the invention will have at least about 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess a desired biological activity of the native protein, particularly, polysaccharide synthesis activity as described herein. Such variants may result from, for example, genetic polymorphism or from human manipulation. Biologically active variants of a native polysaccharide synthase protein of the invention will have at least about 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the polysaccharide synthase polypeptides can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired polysaccharide synthase activity. Obviously, the mutations that will be made in the DNA encoding the variant must not place the sequence out of reading frame and preferably will not create complementary regions that could produce secondary mRNA structure. See EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by UDP-substrate binding studies, including a test battery assay to determine optimal substrates. See, for example, Pear et al. (1996) *Proc. Natl. Acad. Sci.* 93:12637-12642; Geshi et al. (2000) *Planta* 210:622-629; Wulff et al. (2000) *Plant Physiol.* 122:867-877) herein incorporated by reference.

Variant nucleotide sequences and proteins also encompass sequences and proteins derived from a mutagenic and recombinogenic procedure such as DNA shuffling. With such a procedure, one or more different polysaccharide synthase coding sequences can be manipulated to create a new polysaccharide synthase possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a polysaccharide synthase sequences of the invention and other known polysaccharide synthase genes to obtain a new gene coding for a polysacchaide synthase with an improved property of interest, such as an increased $K_m$. Strategies for such DNA shuffling are known in the art. See, for example, Stemmer (1994) *Proc. Nat. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants, and more particularly other monocots. In this manner, methods such as PCR, hybridization, and the like can be used to identify such sequences based on their sequence homology to the sequences set forth herein. Sequences isolated based on their sequence identity to the entire polysaccharide synthase sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polysaccharide synthase sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire polysaccharide synthase sequences disclosed herein, or one or more portions thereof, may be used as a probe capable of specifically hybridizing to corresponding polysaccharide synthase sequences and messenger RNAs. To achieve specific hybridization under a variety of conditions, such probes include sequences that are unique among polysaccharide synthase sequences and are preferably at least about 10 nucleotides in length, and most preferably at least about 20 nucleotides in length. Such probes may be used to amplify corresponding polysaccharide synthase sequences from a chosen plant by PCR. This technique may be used to isolate additional coding sequences from a desired plant or as a diagnostic assay to determine the presence of coding sequences in a desired plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, N.Y.). See Sambrook et al. (1989) *Molecular Cloning: A Laboratory Manual* (2d ed., Cold Spring Harbor Laboratory Press, Plainview, N.Y.).

Thus, isolated sequences that encode for a polysaccharide synthase protein and which hybridize under stringent conditions to the polysaccharide synthase sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably-at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Methods are provided for modulating polysaccharide synthase levels in a plant. By "modulating" is intended decreasing or increasing the native levels of polysaccharide synthase transcripts, polypeptides, enzyme activity; altering the enzyme specificity; or a combination thereof. By "decreasing" polysaccharide synthase transcripts, polypeptides, or enzyme activity is intended a 1%, 5%, 10%, 20%, 30%, 40%, 50%, 60%, 70%, 80%, 90%, 91%, 92%, 93%, 94%, 95%, 96%, 97%, 98%, 99%, 100% reduction of the native polysaccharide transcript, polypeptide or enzyme activity. By "increasing" polysaccharide synthase transcripts, polypeptides, or enzyme activity is intended a 1%, 5%, 10%, 20%, 30%, 40%, 50%, 60%, 70%, 80%, 90%, 91%, 92%, 93%, 94%, 95%, 96%, 97%, 98%, 99%, 100% or more augmentation of the native polysaccharide transcript, polypeptide, or enzyme activity. Modulating also comprises expression of an enzyme normally not found in a particular plant. Thus, plants and plant cells are obtained that have altered polysaccharide biosynthesis pathways. Such plants, plant cells, and plant tissues are "modified" in that the activities of proteins in polysaccharide biosynthesis pathways are altered. As noted below, various methods are available for creating modified plants, plant cells, and plant tissues, including transformation, transcription, and breeding. Any method known in the art for modulating expression may be employed singly or in combination to achieve the desired result. Such techniques will lead to an altered expression of polysaccharide synthase polypeptides involved in the polysaccharide biosynthesis pathways in the modified plant, plant cell, or plant tissue.

Modulating can be accomplished by either up-regulating or down-regulating expression of a nucleotide sequence of the invention. An embodiment of the invention involves modulation of polysaccharide synthase expression in a crop plant, particularly maize. Methods for up-regulating expression of a nucleotide sequence include introducing a nucleotide sequence of the invention operably linked to a heterologous promoter such as a strong promoter, constitutive promoter, or seed-specific promoter into a plant cell of interest. Methods for down-regulating expression of a nucleotide sequence include the use of antisense suppression and co-suppression technology to inhibit expression of a nucleotide sequence of the invention.

Anti-sense suppression technology is a method of down-regulating expression of the nucleotide sequences of the invention. It is recognized that with these nucleotide sequences, antisense constructions complementary to at least a portion of the messenger RNA (mRNA) for the polysaccharide synthase sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisense sequences may be used. Furthermore, portions of the antisense nucleotides may be used to disrupt the expression of the target sequence. Generally, sequences of at least 50 nucleotides, 100 nucleotides, 200 nucleotides, or greater may be used.

The nucleotide sequences of the present invention may also be used in the sense orientation to suppress the expression of endogenous polysaccharide synthases in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See U.S. Pat. Nos. 5,283,184 and 5,034,323; herein incorporated by reference.

Alternatively, polysaccharide synthase expression may be modulated by modifying the kinetic properties of an endogenous polysaccharide synthase through site-directed alterations of the coding sequence of the endogenous gene resulting in changes in the amino acid sequence of the encoded enzyme. Such site-directed alterations may be accomplished by any method known in the art including, but not limited to, a chimeraplasty-based method involving a nucleotide construct of the invention.

In one embodiment of the invention a method for improving the digestibility of grain crops is provided. By "digestibility" is intended the percentage of a substance taken into a digestive tract that is absorbed by the body. Arabinoxylans constitute 45%-65% of the grain cell wall, but they impede digestion of the grain and may sequester digestible components of grain thus reducing digestibility (WO 99/67404; van der Klis etal. (1995) *Anim. Feed Sci. & Tech.* 51:15-27). The high levels of undigestible material contribute to the sanitation challenges of livestock and poultry raising (Selinger et al. (1996) *Anaerobe* 2:263-284). The methods for modulating polysaccharide synthase levels can be used to increase digestibility of grain and forage crops by lowering the concentration of polysaccharide synthases, thereby lowering the concentration of hemicelluloses, such as arabinoxylan, in the modified plant. Tissue-specific promoters can be used to direct down regulation of expression of the nucleotide sequences of the invention in the desired plant tissues using antisense or sense-suppression technology as described elsewhere herein.

Methods to measure digestibility are known in the art and include, but are not limited to, determining the food conversion ratio (WO 99/67404), sampling chyme for chromium, phosphorous, calcium, magnesium, sodium, and potassium (van der Klis et al. (1995) *Anim. Feed Sci. & Tech.* 51:15-27), in sacco degradation (van Vuuren et al. (1989) *Grass & Forage Sci.* 44:223-230), growth studies (GrootWassink et al. (1989) *J. Sci. Food Agric.* 46:289-300), and the enzyme digestible dry matter (EDDM) assay (Boisen and Fernandez (1997) *Animal Feed Sci. Tech.* 68:83-92; and Boisen and Fernandez (1995) *Animal Feed Sci. Tech.* 51 :29-43); all of which are herein incorporated by reference. Such methods can be used to determine the digestibility and/or energy availability of the plant parts of plants modified in accordance with methods of the invention. The modified plant parts, such as modified grain, may be fed to a variety of livestock including, but not limited to, poultry, cattle, swine, horses, and sheep.

In another embodiment of the invention a method for improving gum extractability is provided. By "gum" is intended any of numerous colloidal polysaccharides of plant origin that are gelatinous when moist but which harden on drying, including, but not limited to, arabinoxylans, galactans, and mixed-link glucans. Whereas high gum concentration can be detrimental to digestibility, there is a strong interest in their industrial applications, such as their use as thickeners in the food industry (Sanderson (1982) *Prog. Fd. Nutr. Sci.* 6:77-87). About 15% of the total corn produced in the USA is subjected to wet milling to produce mainly starch and also oil from the germ. Wet milling is a multi-step process involving the steeping and grinding of kernels, and separating the kernels into starch, protein, oil, and fiber portions. See S. R. Eckhoff (1992) Proceedings of the 4$^{th}$ Corn Utilization Conference, Jun. 24-26, 1992, St. Louis, Mo., (National Corn Growers Association, CIBA-GEIGY Seed Division, and the USDA). The fiber residue left at the end of the wet-milling process is rich in arabinoxylans. However, it is not currently economically feasible to extract arabinoxylans from the wet-milled residue of corn. Increasing the level of arabinoxylans, galactans, or mixed-link glucans in the maize grain improves the ability to extract the gums. This can be achieved by generating a plant that overexpresses polysaccharide synthases involved in synthesis of arabinoxylans, galactans, and mixed-link glucans, particularly overexpression in the tissue of interest, such as grain.

The present invention also provides a method for modulating the plant growth rate. Plant cell growth is accomplished through loosening of the plant cell wall and expansion due to the turgor pressure of the plant cell. There is a relationship between the looseness of the plant cell wall and the turgor pressure of the cell such that looser cell walls require less turgor pressure to expand, while stronger cell walls require more turgor pressure to expand. A component of cell wall loosening is the deposition by a process known as intussusception of matrix polysaccharides within the cell wall. The newly incorporated polysaccharides relieve stress in the load-bearing components of the plant cell wall and prevent a perpetual gradual thinning of the cell walls during plant cell growth. Under conditions of drought or stress, the turgor pressure of the cell decreases, and the plant decreases synthesis of the polysaccharides necessary for cell-wall loosening and cell growth (see Ray (1992) *Curr. Topics in Plant Biochem. & Phys.* 11:18-41). In this manner, the interplay between low turgor pressure and the strength of the cell wall prevents or slows growth. Increased synthesis of polysaccharides would allow the plant cell wall to loosen and allow growth with less turgor pressure. The use of stress-responsive promoters would allow regulated expression of the polysaccharide synthases of the invention (see U.S. Patent Nos: U.S. Pat. No. 5,891,859; U.S. Pat. No. 5,929,305; U.S. Pat. No. 5,965,705; U.S. Pat. No. 5,892,009). Polysaccharide synthases of the Csl family of gene products have been shown to be involved in plant growth (Favery et al. (2001) *Genes Dev.* 15:79-89). Therefore, plant cell growth may be modulated by modulating the levels of polysaccharides through modulation of polysaccharide synthase expression. In this manner, the nucleotide sequences of the invention may be used to modulate the levels of polysaccharide synthesis activity and thus to mediate plant growth.

Although modulated growth of the entire plant is one possible desired embodiment, it is recognized that modulated growth of specific tissues such as the roots or seeds may be desired. Methods of tissue-preferred expression of the nucleotide sequences of the invention are discussed elsewhere herein.

The polysaccharide synthase sequences of the invention are provided in expression cassettes for expression in the plant of interest. The cassette will include 5' and 3' regulatory sequences operably linked to a nucleotide sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the polysaccharide synthase sequence to be under the transcriptional regulation of the regulatory regions. The expression cassette may additionally contain selectable marker genes.

The expression cassette will include in the 5'-3' direction of transcription, a transcriptional and translational initiation region, a nucleotide sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region be not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of polysaccharide synthases in the plant or plant cell. Thus, the phenotype of the plant or plant cell is altered.

The termination region may be native with the transcriptional initiation region; may be native with the operably linked polysaccharide synthase sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the polysaccharide synthase sequences may be optimized for increased expression in the transformed plant. That is, the sequences can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred sequences. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, N.Y.), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

In certain embodiments the nucleic acid sequences of the present invention can be stacked with any combination of polynucleotide sequences of interest in order to create plants with a desired phenotype. For example, the polynucleotides of the present invention may be stacked with any other polynucleotides of the present invention, such as any combination of polysaccharide synthases (SEQ ID NOS: 1, 3, 5, 7, 9, 11, 13, 15, 17, 19, 21, 23, 25, 27, 29), or with other genes implicated in polysaccharide synthase enzymatic activities including, but not limited to, xyloglucan alpha 1-2 fucosyltransferase; galactinol synthase; KOJAK; sucrose:sucrose 1-fructosyltransferase; fructan:fructan 1-fructosyltransferase; and Suc:fructan-6-fructosyltransferase. (See Wulff et al. (2000) *Plant Physiol.* 122:867-877; Sprenger et al. (2000) *Plant J.* 21:249-258; Favery et al. (2001) *Genes Dev.* 15:79-89; Reid (2000) *Curr. Opin. Plant Biol.* 3:512-516; Hellwege et al. (2000) *Proc. Natl. Acad. Sci.* 15:8699-8704; Muller et al. (2000) *Plant Physiol.* 123:265-274; Geshi et al. (2000) *Planta* 210:622-629, and U.S. Pat. No. 6,194,638, each of which is herein incorporated by reference.) The combinations generated can also include multiple copies of any one of the polynucleotides of interest. The polynucleotides of the present invention can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703, 409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. application Ser. No. 10/053, 410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366, 892; 5,747,450; 5,737,514; 5,723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529 ); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA of interest. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of a plant of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in a plant, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant*

Cell 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Chemical-regulated promoters can be used to modulate the expression of a gene in a plant through the application of an exogenous chemical regulator. Depending upon the objective, the promoter can be a chemical-inducible promoter, where application of the chemical induces gene expression, or a chemical-repressible promoter, where application of the chemical represses gene expression. For example, a chemically regulated promoter might be used to alter expression of the sequences of the invention prior to harvest. Application prior to harvest might allow the benefits of the invention, including improved digestibility or gum extraction, without impinging normal plant growth or development. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena etal. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target modulation of polysaccharide synthase expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson etal. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see the copending application entitled "Seed-Preferred Promoters," U.S. application Ser. No. 09/377,648, filed Aug. 19, 1999, herein incorporated by reference). Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc.

Root-preferred promoters are known and can be selected from the many available from the literature or isolated de novo from various compatible species. See, for example, Hire et al. (1992) *Plant Mol. Biol.* 20(2): 207-218 (soybean root-specific glutamine synthase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus comiculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179; herein incorporated by reference.

Where low level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompass promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, the copending application entitled "Constitutive Maize Promoters," U.S. application Ser. No. 09/257,584, filed Feb. 25, 1999, and herein incorporated by reference.

Additional examples of promoters include the F3.7 promoter from maize (Baszczynski, et al. (1997) *Maydica* 42:189-201); the soybean albumin promoter (U.S. Pat. No. 6,177,613), the beta conglycinin promoter (WO 91/13993), the Smas promoter, the cinnamyl alcohol dehydrogenase promoter (U.S. Pat. No. 5,683,439), the SCP1 promoter, the Nos promoter, and the rubisco promoter. Yet more examples of promoters include the 1'- or 2'-promoter derived from T-DNA of *Agrobacterium tumefaciens*, the histone H2B promoter (Nakayama et al. (1992) *FEBS Lett* 30:167-170), the GRP1-8 promoter, and other transcription initiation regions from various plant genes known in the art.

Examples of promoters under developmental control include promoters that initiate transcription preferentially in certain tissues, such as leaves, roots, fruits, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, (Boronat et al. (1986) *Plant Sci.* 47:95-102, Reina et al. (1990) *Nucleic Acids Res.* 18:6426, and Kloesgen et al. (1986) *Mol Gen Genet* 203:237-244, each of which is herein incorporated by reference).

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886, 244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407413 (rice); Osjoda etal. (1996) *Nature Biotechnology* 14:745-750 (maize via *Agrobacterium tumefaciens*); all of which are herein incorporated by reference.

The nucleotide constructs of the invention may be introduced into plants by contacting plants with a virus or viral nucleic acids. Generally, such methods involve incorporating a nucleotide construct of the invention within a viral DNA or RNA molecule. It is recognized that a polysaccharide synthase of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889, 190, 5,866,785, 5,589,367 and 5,316,931; herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having the desired type of expression, for example constitutive or tissue-preferred expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The nucleotide sequences encompassed by the present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus* casica), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and muskmelon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

This invention can be better understood by reference to the following non-limited examples. It will be appreciated by those skilled in the art that other embodiments of the invention may be practiced without departing from the spirit and the scope of the invention as herein disclosed.

EXPERIMENTAL

Example 1

Particle Gun Transformation and Regeneration of Transgenic Maize Plants

Immature maize embryos from greenhouse donor plants are bombarded with a plasmid containing a polysaccharide synthase sequence of the invention operably linked to a F3.7 promoter (Baszczynski, et al. (1997) *Maydica* 42:189-201) and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a nucleotide sequence of the invention operably linked to a F3.7 promoter is made. This plasmid DNA plus plasmid DNA containing a PAT selectable marker is precipitated onto 1.1 µm (average diameter) tungsten pellets using a $CaCl_2$ precipitation procedure as follows:
  100 µl prepared tungsten particles in water
  10 µl (1 µg) DNA in Tris EDTA buffer (1 µg total DNA)
  100 µl 2.5 M $CaCl_2$
  10 µl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for altered polysaccharide synthase activity.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I H$_2$O following adjustment to pH 5.8 with KOH); 3.0 g/l Gelrite (added after bringing to volume with D-I H$_2$O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H$_2$O) (Murashige and Skoog (1962) *Physiol. Plant* 15:473), 100 mg/l myo-inositol, 0.5 mg/l zeatin, 60 g/l sucrose, and 1.0 ml/l of 0.1 mM abscisic acid (brought to volume with polished D-I H$_2$O after adjusting to pH 5.6); 3.0 g/l Gelrite (added after bringing to volume with D-I H$_2$O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H$_2$O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H$_2$O), sterilized and cooled to 60° C.

Example 2

*Agrobacterium*-mediated Transformation of Maize

For *Agrobacterium*-mediated transformation of maize with polysaccharide synthase gene(s) or nucleotide sequence(s) of the invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterium, where the bacteria are capable of transferring the polysaccharide synthase gene(s) or nucleotide. sequence(s) to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants. Regenerated transgenic plants are then monitored for altered polysaccharide synthase activity.

Example 3

Soybean Embryo Transformation Example

Soybean embryos are bombarded with a plasmid containing a polysaccharide synthase gene or nucleotide sequence of the invention operably linked to a soybean albumin promoter (U.S. Pat. No. 6,177,613) as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising a polysaccharide synthase nucleotide sequence operably linked to the soybean albumin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos. Regenerated transgenic plants are then monitored for altered polysaccharide synthase activity.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated nucleic acid molecule comprising a nucleotide sequence selected from the group consisting of:
   a) a nucleotide sequence comprising the sequence set forth in SEQ ID NO: 21; and
   b) a nucleotide sequence encoding a polypeptide having the amino acid sequence set forth in SEQ ID NO: 22.

2. An expression cassette comprising a nucleotide sequence of claim 1, wherein said nucleotide sequence is operably linked to a promoter that drives expression in a plant.

3. A plant cell having stably incorporated into its genome an expression cassette of claim 2.

4. A plant having stably incorporated in its genome an expression cassette of claim 2.

5. The plant of claim 4, wherein said plant is a dicot.

6. The plant of claim 4, wherein said plant is a monocot.

7. Transformed seed of a plant of claim 4.

8. A method for decreasing the level of a polysaccharide synthase in a plant, the method comprising stably transforming a plant cell with a nucleotide sequence operably linked to a heterologous promoter capable of initiating transcription in a plant, and regenerating a transformed plant, wherein said nucleotide sequence comprises a nucleotide sequence selected from the group consisting of:
   a) a nucleotide sequence comprising the sequence set forth in SEQ ID NO: 21; and
   b) a nucleotide sequence encoding a polypeptide having the amino acid sequence set forth in SEQ ID NO: 22.

9. The method of claim 8, wherein said plant is a dicot.

10. The method of claim 8, wherein said plant is a monocot.

* * * * *